(12) United States Patent
Rafi et al.

(10) Patent No.: US 11,253,361 B2
(45) Date of Patent: Feb. 22, 2022

(54) HEART VALVE PINCH DEVICES AND DELIVERY SYSTEMS

(71) Applicant: Edwards Lifesciences Corporation, Irvine, CA (US)

(72) Inventors: Hamid Rafi, Irvine, CA (US); Russell T. Joseph, Las Flores, CA (US); Robert Bowes, Trabuco Canyon, CA (US); Uy D. Trinh, Garden Grove, CA (US); Emil Karapetian, Huntington Beach, CA (US); Gregory Bak-Boychuk, San Clemente, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 89 days.

(21) Appl. No.: 16/508,625

(22) Filed: Jul. 11, 2019

(65) Prior Publication Data

US 2019/0328512 A1    Oct. 31, 2019

Related U.S. Application Data

(63) Continuation of application No. 15/703,888, filed on Sep. 13, 2017, now Pat. No. 10,357,361.

(Continued)

(51) Int. Cl.
*A61F 2/24* (2006.01)
*A61F 2/95* (2013.01)

(52) U.S. Cl.
CPC ............ *A61F 2/243* (2013.01); *A61F 2/2418* (2013.01); *A61F 2/2436* (2013.01); *A61F 2/2442* (2013.01);

(Continued)

(58) Field of Classification Search
CPC .... A61F 2/2418; A61F 2/2436; A61F 2/9517; A61F 2/2442; A61F 2/243–4329
See application file for complete search history.

(56) References Cited

U.S. PATENT DOCUMENTS 4,035,849 A    7/1977  Angell et al.
4,592,340 A    6/1986  Boyles
(Continued)

FOREIGN PATENT DOCUMENTS

CN    102395331 A    3/2012
CN    102958469 A    3/2013
(Continued)

*Primary Examiner* — Brian A Dukert
*Assistant Examiner* — Rebecca Lynee Zimmerman
(74) *Attorney, Agent, or Firm* — Edwards Lifesciences

(57) ABSTRACT

Pinch devices and access systems that can be used to secure a prosthetic heart valve to a heart valve annulus and to treat valvular insufficiency. A pinch device can be a separate expandable element from the prosthetic heart valve that is first advanced to the annulus and deployed, after which an expandable prosthetic heart valve can be advanced to within the annulus and deployed. The two elements can clamp/pinch the heart valve leaflets to hold the prosthetic heart valve in place. The pinch device can have a flexible, expandable annular frame. A combined delivery system can deliver the pinch device and prosthetic heart valve with just a single access point and aid more accurate coaxial deployment. The pinch device can be mounted near distal end of an access sheath, and a catheter for delivering the prosthetic heart valve can be passed through a lumen of the same access sheath.

20 Claims, 11 Drawing Sheets

Related U.S. Application Data

(60) Provisional application No. 62/395,283, filed on Sep. 15, 2016.

(52) U.S. Cl.
CPC ..... *A61F 2/9517* (2020.05); *A61F 2210/0014* (2013.01); *A61F 2230/0054* (2013.01); *A61F 2230/0063* (2013.01); *A61F 2250/006* (2013.01); *A61F 2250/0063* (2013.01)

(56) References Cited

U.S. PATENT DOCUMENTS

| | | | |
|---|---|---|---|
| 4,994,077 A | 2/1991 | Dobben | |
| 5,059,177 A | 10/1991 | Towne et al. | |
| 5,411,552 A | 5/1995 | Andersen et al. | |
| 5,554,185 A | 9/1996 | Block et al. | |
| 5,591,195 A | 1/1997 | Taheri et al. | |
| 5,599,305 A | 2/1997 | Hermann et al. | |
| 5,639,274 A | 6/1997 | Fischell et al. | |
| 5,728,068 A | 3/1998 | Leone et al. | |
| 5,840,081 A | 11/1998 | Andersen et al. | |
| 5,968,068 A | 10/1999 | Dehdashtian et al. | |
| 6,168,614 B1 | 1/2001 | Andersen et al. | |
| 6,217,585 B1 | 4/2001 | Houser et al. | |
| 6,379,372 B1 | 4/2002 | Dehdashtian et al. | |
| 6,419,696 B1 | 7/2002 | Ortiz et al. | |
| 6,432,134 B1 | 8/2002 | Anson et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,527,979 B2 | 3/2003 | Constantz et al. | |
| 6,582,462 B1 | 6/2003 | Andersen et al. | |
| 6,652,578 B2 | 11/2003 | Bailey et al. | |
| 6,730,118 B2 | 5/2004 | Spenser et al. | |
| 6,730,121 B2 | 5/2004 | Ortiz et al. | |
| 6,733,525 B2 | 5/2004 | Yang et al. | |
| 6,767,362 B2 | 7/2004 | Schreck | |
| 6,797,002 B2 | 9/2004 | Spence et al. | |
| 6,830,584 B1 | 12/2004 | Seguin | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,018,408 B2 | 3/2006 | Bailey et al. | |
| 7,037,334 B1 | 5/2006 | Hlavka et al. | |
| 7,077,861 B2 | 7/2006 | Spence | |
| 7,101,395 B2 | 9/2006 | Tremulis et al. | |
| 7,125,421 B2 | 10/2006 | Tremulis et al. | |
| 7,276,084 B2 | 10/2007 | Yang et al. | |
| 7,318,278 B2 | 1/2008 | Zhang et al. | |
| 7,374,571 B2 | 5/2008 | Pease et al. | |
| 7,393,360 B2 | 7/2008 | Spenser et al. | |
| 7,510,575 B2 | 3/2009 | Spenser et al. | |
| 7,585,321 B2 | 9/2009 | Cribier | |
| 7,618,446 B2 | 11/2009 | Andersen et al. | |
| 7,737,060 B2 | 6/2010 | Strickler et al. | |
| 7,785,366 B2 | 8/2010 | Maurer et al. | |
| 7,951,195 B2 | 5/2011 | Antonsson et al. | |
| 8,029,556 B2 | 10/2011 | Rowe | |
| 8,167,932 B2 | 5/2012 | Bourang et al. | |
| 8,323,335 B2 | 12/2012 | Rowe et al. | |
| 8,377,115 B2 | 2/2013 | Thompson | |
| 8,398,708 B2 | 3/2013 | Meiri et al. | |
| 8,449,605 B2 | 5/2013 | Lichtenstein et al. | |
| 8,449,606 B2 | 5/2013 | Eliasen et al. | |
| 8,540,767 B2 | 9/2013 | Zhang | |
| 8,657,872 B2 | 2/2014 | Seguin | |
| 8,663,322 B2 | 3/2014 | Keranen | |
| 8,672,998 B2 | 3/2014 | Lichtenstein et al. | |
| 8,734,507 B2 | 5/2014 | Keranen | |
| 9,078,747 B2 | 7/2015 | Conklin | |
| 9,095,434 B2 | 8/2015 | Rowe | |
| 9,119,718 B2 | 9/2015 | Keranen | |
| 9,237,886 B2 | 1/2016 | Seguin et al. | |
| 9,364,326 B2 | 6/2016 | Yaron | |
| 9,463,268 B2 | 10/2016 | Spence | |
| 9,474,599 B2 | 10/2016 | Keranen | |
| 9,622,863 B2 | 4/2017 | Karapetian et al. | |
| 2002/0032481 A1 | 3/2002 | Gabbay | |
| 2003/0050694 A1 | 3/2003 | Yang et al. | |
| 2003/0225420 A1 | 12/2003 | Wardle | |
| 2004/0133263 A1 | 7/2004 | Dusbabek et al. | |
| 2004/0186565 A1 | 9/2004 | Schreck | |
| 2004/0260389 A1 | 12/2004 | Case et al. | |
| 2005/0096736 A1 | 5/2005 | Osse et al. | |
| 2005/0119735 A1 | 6/2005 | Spence et al. | |
| 2005/0182486 A1 | 8/2005 | Gabbay | |
| 2005/0203614 A1 | 9/2005 | Forster et al. | |
| 2005/0203617 A1 | 9/2005 | Forster et al. | |
| 2006/0025857 A1 | 2/2006 | Bergheim et al. | |
| 2006/0229561 A1 | 10/2006 | Huszar | |
| 2007/0005131 A1 | 1/2007 | Taylor | |
| 2007/0010877 A1 | 1/2007 | Salahieh et al. | |
| 2007/0203575 A1 | 8/2007 | Forster et al. | |
| 2007/0265700 A1 | 11/2007 | Eliasen et al. | |
| 2008/0033542 A1 | 2/2008 | Antonsson et al. | |
| 2008/0125853 A1 | 5/2008 | Bailey et al. | |
| 2008/0208330 A1 | 8/2008 | Keranen | |
| 2008/0294230 A1 | 11/2008 | Parker | |
| 2009/0157175 A1 | 6/2009 | Benichou | |
| 2009/0240320 A1 | 9/2009 | Tuval et al. | |
| 2009/0276040 A1 | 11/2009 | Rowe et al. | |
| 2009/0281619 A1 | 11/2009 | Le et al. | |
| 2009/0319037 A1 | 12/2009 | Rowe et al. | |
| 2010/0049313 A1 | 2/2010 | Alon et al. | |
| 2010/0145440 A1 | 6/2010 | Keranen | |
| 2010/0198347 A1 | 8/2010 | Zakay et al. | |
| 2010/0312333 A1 | 12/2010 | Navia et al. | |
| 2010/0318184 A1 | 12/2010 | Spence | |
| 2011/0015729 A1 | 1/2011 | Jimenez et al. | |
| 2012/0022633 A1* | 1/2012 | Olson | A61F 2/2418 623/1.11 |
| 2012/0059458 A1 | 3/2012 | Buchbinder et al. | |
| 2012/0123529 A1 | 5/2012 | Levi et al. | |
| 2012/0283820 A1 | 11/2012 | Tseng et al. | |
| 2013/0268049 A1* | 10/2013 | Munsinger | A61F 2/966 623/1.11 |
| 2013/0317598 A1 | 11/2013 | Rowe et al. | |
| 2014/0031926 A1 | 1/2014 | Kudlik et al. | |
| 2014/0052240 A1* | 2/2014 | Zhang | A61F 2/2418 623/2.11 |
| 2014/0172070 A1 | 6/2014 | Seguin | |
| 2014/0379074 A1 | 12/2014 | Spence et al. | |
| 2015/0148896 A1 | 5/2015 | Karapetian et al. | |
| 2015/0230921 A1 | 8/2015 | Chau et al. | |
| 2015/0282931 A1 | 10/2015 | Brunnett et al. | |
| 2015/0335428 A1 | 11/2015 | Keranen | |
| 2015/0374493 A1 | 12/2015 | Yaron et al. | |
| 2016/0074165 A1 | 3/2016 | Spence et al. | |
| 2016/0095705 A1 | 4/2016 | Keranen et al. | |
| 2016/0184095 A1 | 6/2016 | Spence et al. | |
| 2016/0199177 A1 | 7/2016 | Spence et al. | |
| 2016/0228248 A1 | 8/2016 | Rowe et al. | |
| 2016/0256276 A1 | 9/2016 | Yaron | |
| 2017/0007399 A1 | 1/2017 | Keranen | |
| 2017/0007402 A1 | 1/2017 | Zerkowski et al. | |
| 2017/0217385 A1 | 8/2017 | Rinkleff et al. | |
| 2018/0183194 A1 | 6/2018 | Wang | |

FOREIGN PATENT DOCUMENTS

| | | |
|---|---|---|
| DE | 19532846 A1 | 3/1997 |
| DE | 19907646 A1 | 8/2000 |
| EP | 0592410 A1 | 4/1994 |
| EP | 0850607 A1 | 7/1998 |
| EP | 1432369 A1 | 6/2004 |
| EP | 1521550 A2 | 4/2005 |
| EP | 1796597 A2 | 6/2007 |
| EP | 1296618 B1 | 1/2008 |
| EP | 1827314 B1 | 12/2010 |
| EP | 2620125 A1 | 7/2013 |
| EP | 2726018 A2 | 5/2014 |
| EP | 2806829 A2 | 12/2014 |
| FR | 2815844 A1 | 5/2002 |

(56) References Cited

FOREIGN PATENT DOCUMENTS

| | | | |
|---|---|---|---|
| WO | 9117720 | A1 | 11/1991 |
| WO | 9829057 | A1 | 7/1998 |
| WO | 0149213 | A2 | 7/2001 |
| WO | 0154625 | A1 | 8/2001 |
| WO | 0176510 | A2 | 10/2001 |
| WO | 0222054 | A1 | 3/2002 |
| WO | 0236048 | A1 | 5/2002 |
| WO | 0247575 | A2 | 6/2002 |
| WO | 03047468 | A1 | 6/2003 |
| WO | 2005084595 | A1 | 9/2005 |
| WO | 2006011127 | A2 | 2/2006 |
| WO | 2006111391 | A1 | 10/2006 |
| WO | 2006138173 | A2 | 12/2006 |
| WO | 2005102015 | A3 | 4/2007 |
| WO | 2007047488 | A2 | 4/2007 |
| WO | 2007067942 | A1 | 6/2007 |
| WO | 2008112237 | A2 | 9/2008 |
| WO | 2010121076 | A2 | 10/2010 |
| WO | 2013110722 | A2 | 8/2013 |
| WO | 2013114214 | A2 | 8/2013 |
| WO | 2015023579 | A1 | 2/2015 |
| WO | 2015023862 | A2 | 2/2015 |
| WO | 2015127264 | A1 | 8/2015 |
| WO | 2015198125 | A1 | 12/2015 |
| WO | 2016038017 | A1 | 3/2016 |
| WO | 2016040881 | A1 | 3/2016 |
| WO | 2016130820 | A1 | 8/2016 |
| WO | 2017066889 | A1 | 4/2017 |

* cited by examiner

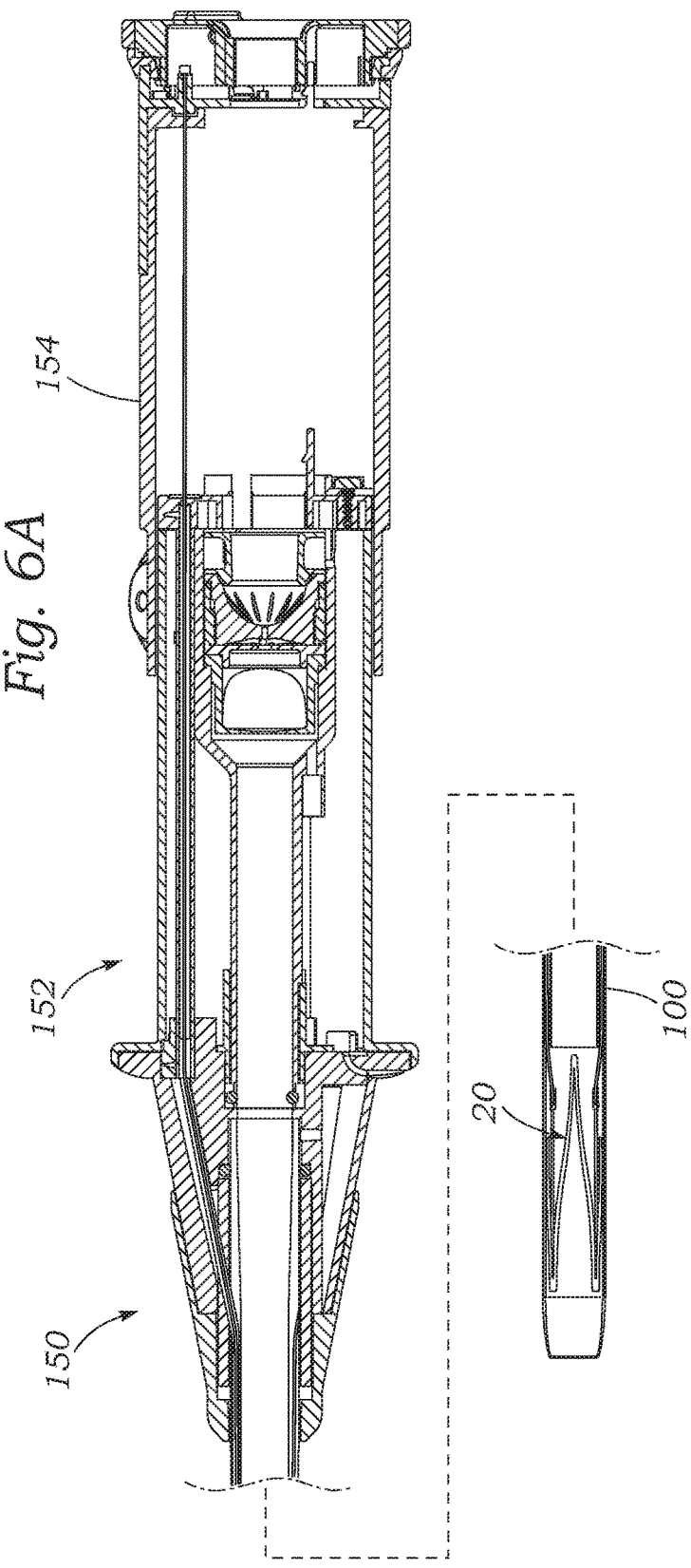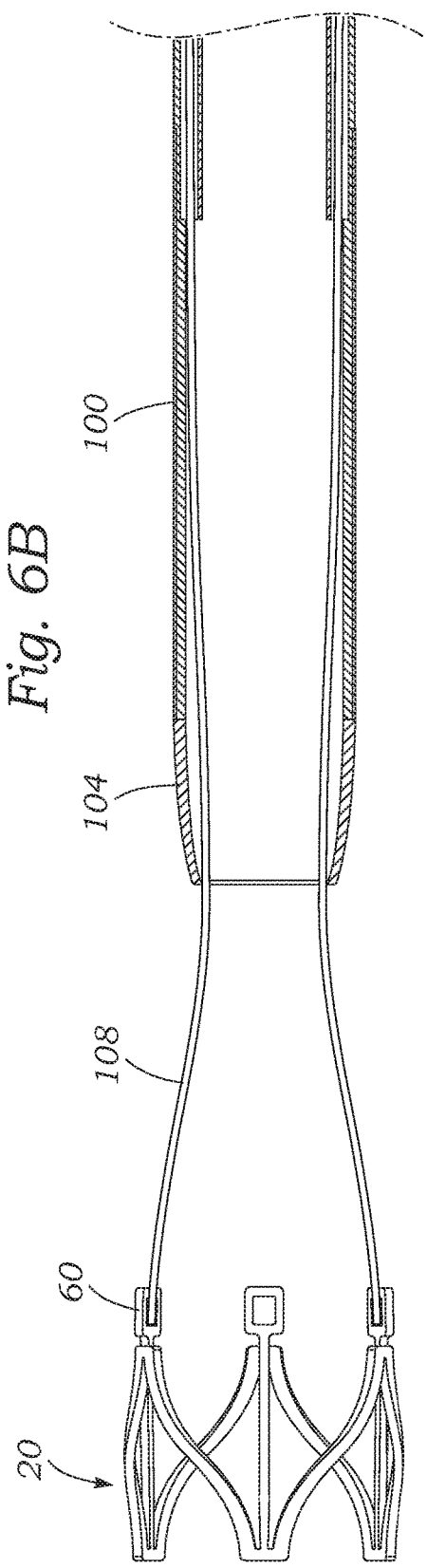

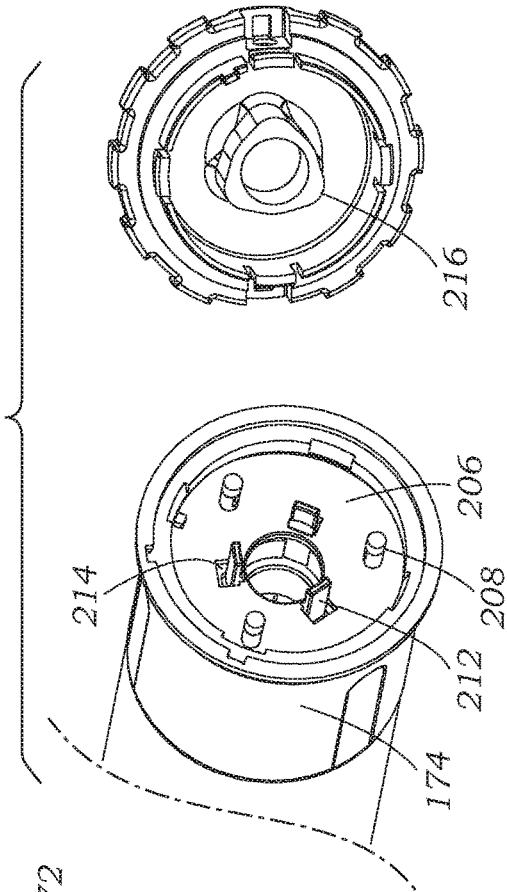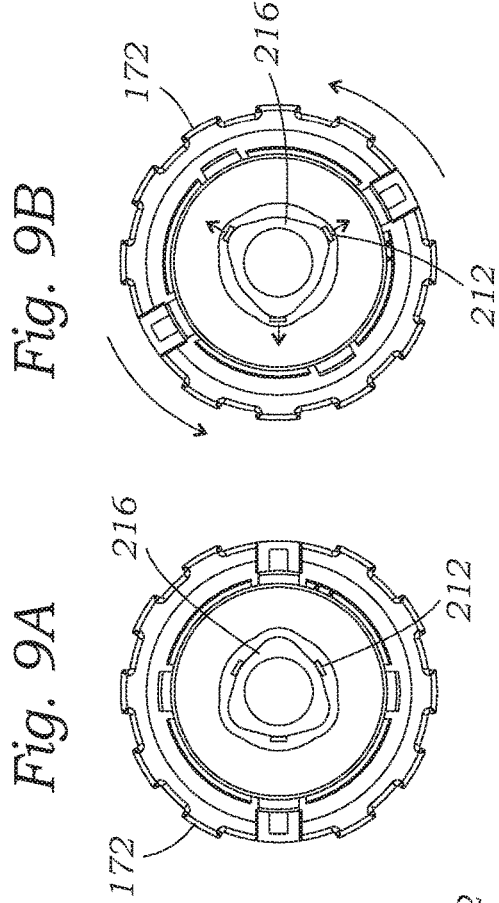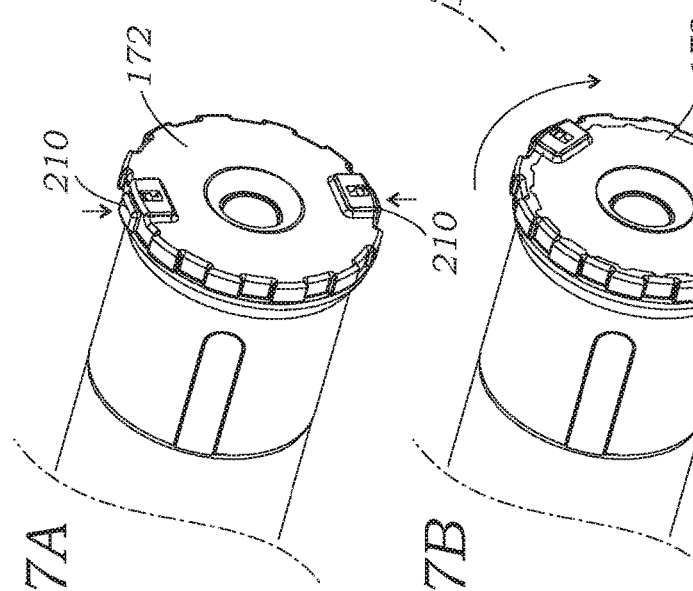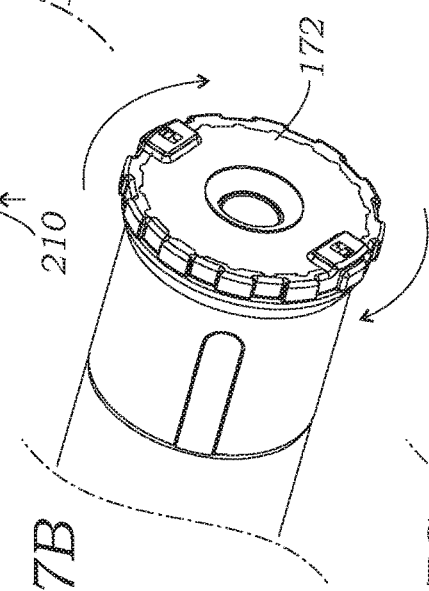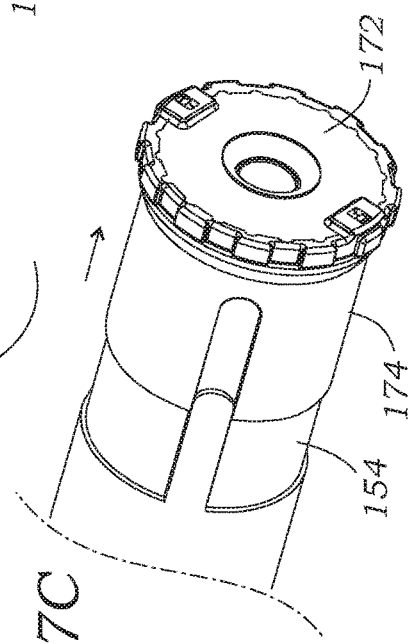

HEART VALVE PINCH DEVICES AND DELIVERY SYSTEMS

RELATED APPLICATIONS

This application is a continuation of U.S. patent application Ser. No. 15/703,888 filed Sep. 13, 2017, which claims the benefit of U.S. Provisional Application No. 62/395,283, filed Sep. 15, 2016, both of which applications are incorporated herein by reference.

FIELD OF THE INVENTION

The present invention relates to heart valve repair, including heart valve repair using a heart valve pinch device and corresponding delivery system and method.

BACKGROUND OF THE INVENTION

The heart is a hollow muscular organ having four pumping chambers separated by four heart valves: aortic, mitral (or bicuspid), tricuspid, and pulmonary. Heart valves are comprised of a dense fibrous ring known as the annulus, and leaflets or cusps attached to the annulus.

Prosthetic heart valves can be used to treat cardiac valvular disorders. The native heart valves (such as the aortic, pulmonary, tricuspid, and mitral valves) serve critical functions in assuring the forward flow of an adequate supply of blood through the cardiovascular system. These heart valves can be rendered less effective by congenital, inflammatory, or infectious conditions. Such conditions can eventually lead to serious cardiovascular compromise or death. It is possible to surgically repair or replace the valve during open heart surgery, where a prosthetic valve is sutured in place, but such surgeries are time-consuming, dangerous and prone to complication.

Transvascular and transapical techniques can be used for introducing and implanting a prosthetic heart valve using a flexible catheter in a manner that is less invasive than open heart surgery. In these techniques, a prosthetic valve can be mounted in a crimped state on the end portion of a flexible catheter and advanced through a blood vessel of the patient until the valve reaches the implantation site. The valve at the catheter tip can then be expanded to its functional size at the site of the defective native valve, such as by inflating a balloon on which the valve is mounted. Alternatively, the valve can have a resilient, self-expanding stent or frame that expands the valve to its functional size when it is advanced from a delivery sheath at the distal end of the catheter. These are sutureless techniques which greatly reduces the procedure time.

Balloon-expandable valves can be used for treating heart valve stenosis, a condition in which the leaflets of a valve (e.g., an aortic valve) become hardened with calcium. The hardened leaflets provide a good support structure on which the valve can be anchored within the valve annulus. Further, the catheter balloon can apply sufficient expanding force to anchor the frame of the prosthetic valve to the surrounding calcified tissue. There are several heart conditions, however, that do not involve hardened valve leaflets but which are still desirably treated by valve replacement. For example, aortic insufficiency (or aortic regurgitation) occurs when an aortic valve does not close properly, allowing blood to flow back into the left ventricle. One cause for aortic insufficiency is a dilated aortic annulus, which prevents the aortic valve from closing tightly. In such cases, the leaflets are usually too soft to provide sufficient support for a balloon-expandable prosthetic valve. Additionally, the diameter of the aortic annulus may continue to vary over time, making it dangerous to install a prosthetic valve that is not reliably secured in the valve annulus. Similar problems can occur with other heart valves as well. For example, mitral insufficiency (or mitral regurgitation) involves these same conditions but affects the mitral valve.

Self-expanding prosthetic valves can suffer from other problems. For example, if a self-expanding prosthetic valve is placed within the patient's defective heart valve (e.g., the aorta or mitral valve), it could continues to exert an outward force on the valve annulus. This continuous outward pressure could cause the valve annulus to dilate further, exacerbating the condition the valve was intended to treat. Additionally, when implanting a self-expanding valve, the outward biasing force of the valve's frame could cause the valve to be ejected very quickly from the distal end of a delivery sheath. This makes delivery of the valve very difficult and dangerous to the patient.

The size of the prosthetic valve to be implanted into a patient can also be problematic when treating aortic or mitral insufficiency. Specifically, the size of a prosthetic valve used to treat aortic or mitral insufficiency would generally need to be larger than a prosthetic valve used to treat aortic or mitral stenosis. This larger valve size can make the delivery procedure much more difficult and dangerous to the patient.

Another potential issue with sutureless valves is valve migration. For example, when an aortic prosthetic valve is implanted, 100-200 mmHg pressure loads on the aortic valve immediately. The pressure times the valve surface area produces a substantial load force on the prosthetic valve and could cause valve migration towards the aortic arch. Another potential cause of valve migration is a tilted valve landing. When tilted, the prosthetic valve will have a larger surface area facing the blood flow, which could push the prosthetic valve into the aorta.

Treatment of the mitral valve can present additional challenges, and methods and an apparatus appropriate for the aortic valve may not be well suited for use with the mitral valve. For instance, the mitral valve includes clusters of chordae tendineae extending from the valve leaflets to the walls of the ventricle that may interfere with placement of the prosthesis. The shape of the mitral valve, rather than being circular and uniform like the aortic valve, can be an oval or kidney-like shape that may not be well suited for supporting conventional stents of cylindrical configuration. Further, whereas the aortic valve annulus is often entirely surrounded by muscular tissue, the mitral valve annulus may be bounded by muscular tissue on the outer (posterior) wall only. The anterior side of the mitral valve annulus is bounded by a thin vessel wall adjacent the left ventricular outflow tract ("LVOT"), which must remain open to allow blood to pass into the aorta. As a result, the stent-type fixation may not be suitable for the mitral valve because the anterior side of the native valve has insufficient radial strength and can distort, risking occlusion of the left ventricular outflow tract. Moreover, mitral valve disease often is accompanied by (or caused by) gradual enlargement of the native annulus and/or the left ventricle. Thus, treatment approaches which rely upon radial engagement with or outward compression against the native annulus are subject to failure as the size and shape of the annulus changes.

There is a need for improved methods, systems, and apparatus for delivering expandable prosthetic heart valves (e.g., balloon-expandable or self-expandable prosthetic valves). Embodiments of the methods, systems, apparatus, devices, components, etc. disclosed herein can be used to replace native heart valves even when they do not have calcified leaflets (e.g., aortic valves suffering from aortic insufficiency).

SUMMARY OF THE INVENTION

Among other things, the present application discloses embodiments of a pinch device used to secure a prosthetic heart valve to a heart valve annulus. The pinch device can also be termed a grip, a dock, a constrictor, etc., and can comprise a separate expandable element that is first advanced to the heart valve annulus and deployed, after which an expandable heart valve is advanced to the annulus and deployed. The combination of the two elements applies a clamping/pinching force to the heart valve leaflets which holds the prosthetic heart valve in place.

The pinch device embodiments herein can be used with a number of expandable heart valves having either self- or mechanically- or balloon-expandable support frames. The system formed by the prosthetic heart valve and pinch device may be implanted at any of the native heart valves, for example, the aortic and mitral heart valves.

The pinch device can be a flexible, self-expandable annular stent-like frame. The frame can have a continuous undulating shape with peaks and valleys. While various numbers of peaks and valleys can be used, in one embodiment, there are at least three and up to six peaks and three valleys. The pinch device can be made of a super-elastic metallic alloy such as Nitinol, or a similar expedient.

A deployment or delivery system can include a tubular access/delivery sheath. The access/delivery sheath can have a pinch device (e.g., any of the pinch devices described in this disclosure) mounted near the distal end thereof. The access/delivery sheath can also include a lumen through which a catheter for delivering the prosthetic heart valve is passable. This combined delivery system for the pinch device and prosthetic heart valve requires just a single access point, and the prosthetic heart valve remains coaxial to the pinch device for more precise deployment therein.

An exemplary prosthetic heart valve system or prosthetic heart valve and delivery system can comprise a variety of features and components. For example, the system can include an expandable prosthetic heart valve having a constricted diameter and an expanded diameter. The system can also include a delivery catheter having a distal end on or in which the heart valve is mounted. The system can also include a pinch device separate from the heart valve that has an expanded state defining an annular frame formed around a central axis. The frame can have peaks and valleys (e.g., 2-12 peaks and/or 2-12 valleys) extending in opposite axial directions around its periphery.

The pinch device can include a super-elastic inner body or frame. The body/frame can be fully or partially covered with a biocompatible fabric covering. The body/frame can have a plurality of buckles integrated with the inner body/frame, and the plurality of buckles can project from a proximal end (or distal end) with or without any fabric covering. The pinch device in its expanded state can be sized slightly smaller than the expanded diameter of the heart valve.

The system can include an access system, and the access system can have a proximal handle and a distal access sheath. The handle and sheath can define a common lumen sized for passage therethrough of the distal end of the delivery catheter with the heart valve in its constricted diameter thereon. The handle can include one or more hemostatic seals to prevent blood leakage proximally past the distal end of the delivery catheter during use, e.g., as the delivery catheter passes through the lumen of the handle and sheath. The access system can further include a plurality of deployment arms fixed or axially movable therein, and each deployment arm can be coupled to one of the buckles of the pinch device. The pinch device can be positioned in a constricted state within a distal end of the access sheath and can be located distal with respect to the distal end of the delivery catheter, such that the pinch device can be expelled from the access sheath and self-expand prior to the heart valve by distal advancement of the deployment arms and/or retraction of the sheath.

The distal access sheath can be sized and configured to be introduced into the heart and advanced so that the distal end thereof is adjacent a native heart valve, whereupon the pinch device can be expelled therefrom and positioned around native heart valve leaflets and the delivery catheter can be advanced to position the heart valve within the native heart valve leaflets such that expansion of the heart valve pinches the leaflets between the heart valve and pinch device.

Methods of using the various systems and/or devices herein and methods of treating native heart valves (e.g., valvular insufficiency) can include any of the steps described in this disclosure. For example, a beating heart method can include forming a single access point, for example through the mid-sternum area and into the left ventricle adjacent the apex of the heart. Alternatively, the single access point may be formed in the upper leg and into the femoral artery. After appropriate puncturing, widening/dilating, and sealing the access point, a tubular access sheath can be introduced and advanced into proximity with the native heart valve being replaced. For instance, the access sheath can be advanced into the left ventricle and through the aortic valve such that a distal end is positioned in the ascending aorta. A pinch device can then be expelled from the distal end of the access sheath and permitted to expand. Retraction of the access sheath can cause or permit the pinch device to seat against the aortic valve outside (e.g., partially or fully outside) of the aortic leaflets.

The pinch device can be desirably held by elongated arms (e.g., three elongated arms, 2-9 elongated arms, etc.) extending from the access sheath. The arms can be spaced apart (e.g., three arms spaced 120° apart, two arms spaced 180° apart, or in other spacing arrangements such that the arms can pass between native leaflets at commissures). In one embodiment, three arms can be spaced about 120° apart (e.g., ±5°) and can be configured to and/or positioned such that they pass between the aortic leaflets in the commissure regions. Consequently, the aortic valve can continue to function during the procedure.

A replacement prosthetic heart valve can then be advanced through the access sheath and within the aortic leaflets. The health care provider (e.g., doctor, surgeon, etc.) can expand the heart valve either by releasing it from a constraining sheath or by outward expansion with a balloon or mechanically, for example. Expansion of the heart valve traps aortic leaflets between it and the surrounding pinch device. The deployment arms can then be released from engagement with the pinch device, and the access sheath and delivery components removed from the body. A similar procedure can be performed to replace the mitral valve, and either procedure can be accomplished using different access points such as a percutaneous route through the femoral artery.

Methods, e.g., beating heart methods of delivering a prosthetic heart valve through a single access point, can comprise first providing or obtaining an access/delivery system including a proximal handle and a distal access sheath. The handle and sheath can define a common lumen. At the distal end of the access system and sheath can be provided a pinch device in a constricted state, wherein the pinch device has an expanded state defining an annular frame. The pinch device can be the same as or similar to other pinch devices described in this disclosure. The frame of the pinch device can be formed around a central axis having peaks and valleys (e.g., 2-12 peaks and 2-12 valleys) extending in opposite axial directions around its periphery. The pinch device can include a super-elastic inner body/frame, and can be covered (e.g., fully or partially) with a biocompatible fabric covering. The pinch device or inner body/frame can include a plurality of buckles integrated with the inner body/frame. The buckles can project from a proximal end with or without any fabric covering (e.g., the biocompatible fabric covering can extend over all or a portion of the buckles, or not extend to the buckles). The access system can further include a plurality of deployment arms fixed or axially movable therein. Each arm can be coupled to one of the buckles of the pinch device. The pinch device can be positioned in a constricted state within a distal end of the access sheath, and the pinch device can thus be expelled from the access sheath and self-expand by distal advancement of the deployment arms and/or retraction of the sheath.

The methods can further involve inserting a delivery catheter having an expandable prosthetic heart valve mounted on a distal end into the common lumen from the handle. The prosthetic heart valve can be the same as or similar to other prosthetic heart valves described in this disclosure. For example, the prosthetic heart valve can have a constricted diameter and an expanded diameter, and the delivery catheter and prosthetic heart valve in its constricted diameter can be sized to pass entirely through the common lumen and within the deployment arms. The expanded diameter of the prosthetic heart valve can be slightly larger than a diameter of the pinch device in its expanded state to improve retention.

While the heart is beating, an access incision can be formed to gain access to a heart chamber, and the access sheath can be advanced through the access incision until the distal end of the sheath is located adjacent or proximate a native heart valve annulus. The health care provider (e.g. doctor, physician, surgeon, etc.) can expel the pinch device from the access sheath, e.g., by distal advancement of the deployment arms and/or retraction of the sheath, such that the pinch device is unconstrained and self-expands to its expanded state. The health care provider can then position the expanded pinch device around native heart valve leaflets. The delivery catheter can be advanced though the access system to position the prosthetic heart valve within the native heart valve leaflets and within the pinch device. The prosthetic heart valve can be expanded to pinch the native heart valve leaflets between the prosthetic heart valve and pinch device, and the deployment arms can be decoupled from the buckles to release the pinch device.

An exemplary pinch device for securing a prosthetic heart valve to native heart valve leaflets, can comprise a device that has a constricted state and an expanded state defining an annular frame. The annular frame can be formed around a central axis and can have peaks and valleys extending in opposite axial directions around its periphery. The peaks of the pinch device can project in a distal direction and the valleys can project in a proximal direction. The pinch device can include a super-elastic inner body covered with a biocompatible fabric and the inner body can include a plurality of buckles with or without any fabric covering. The buckles can be located at terminal ends of three fingers extending in a proximal direction or distal direction from three of the peaks of the pinch device. The fingers and buckles can be distributed evenly or asymmetrically around a periphery of the pinch device. The pinch device can be sized slightly smaller than an expanded diameter of a heart valve, such that the pinch device can be expanded and positioned around native heart valve leaflets, and expansion of the heart valve within the leaflets pinches the leaflets between the heart valve and pinch device. The inner body can include circumferential struts connecting each two adjacent peaks and valleys. The struts can be a variety of shapes and sizes. In one embodiment, each strut is generally S-shaped, with two curvatures separated by a point of inflection. Each of the circumferential struts can terminate at its corresponding peak and valley in an asymptotic manner such that it is nearly aligned or parallel with the vertical Z-axis.

The various systems and devices described above can include features and components from other systems and devices described elsewhere herein and certain features/components described above can be omitted. Similarly methods described above can include additional steps described elsewhere herein and certain steps described above can be omitted.

Other features and advantages of the present invention will become apparent from the following detailed description, taken in conjunction with the accompanying drawings which illustrate, by way of example, the principles of the invention.

BRIEF DESCRIPTION OF THE DRAWINGS

FIG. 6A is a broken vertical sectional view through the exemplary access/delivery system including the access/delivery sheath with an exemplary pinch device therein and a proximal handle;

FIG. 6B is a vertical sectional view through a distal end of the access sheath after expulsion of the pinch device therefrom but before decoupling of the deployment arms;

FIGS. 7A-7C are enlarged views of a proximal end of the access system handle showing operation of an arm decoupling assembly;

FIG. 8 is an exploded perspective view of the proximal end of the access system handle showing an inner face of an end cap thereof; and FIGS. 9A and 9B are elevational views of the end cap inner face relative to a plurality of locking tabs in the handle in two different rotational orientations.

DETAILED DESCRIPTION OF PREFERRED EMBODIMENTS

Disclosed herein are representative embodiments of a pinch device (sometimes referred to as a "grip," "dock," "constrictor," etc.) that can be used to secure a prosthetic heart valve within a native heart valve. For illustrative purposes, embodiments of the pinch device are described as being used to secure an expandable heart valve such as a transcatheter heart valve ("THV") in the aortic valve or the mitral valve of a heart. The annular pinch device surrounds native heart valve leaflets and the heart valve is expanded within the leaflets so as to "pinch" the leaflets therebetween. It should be understood that the disclosed pinch device and THV can be configured for use with any native heart valve. Also disclosed herein are exemplary methods and systems for deploying the pinch device and corresponding THV, e.g., in a coordinated manner using a single access point.

The pinch device is desirably used in connection with embodiments of a balloon-expandable THV such as the Edwards SAPIEN 3 Transcatheter Heart Valve made by Edwards Lifesciences of Irvine, Calif., or such as described in U.S. Pat. No. 6,730,118, which is hereby expressly incorporated herein by reference. However, these exemplary THVs should not be construed as limiting, and embodiments of the disclosed pinch device can be used to secure a wide variety of THVs delivered through a variety of mechanisms (e.g., self-expanding heart valves, mechanically-expandable heart valves, other balloon-expanding heart valves, combinations of these, and the like). The term, "expandable heart valves" is intended to encompass all such varieties.

Figure 1A:
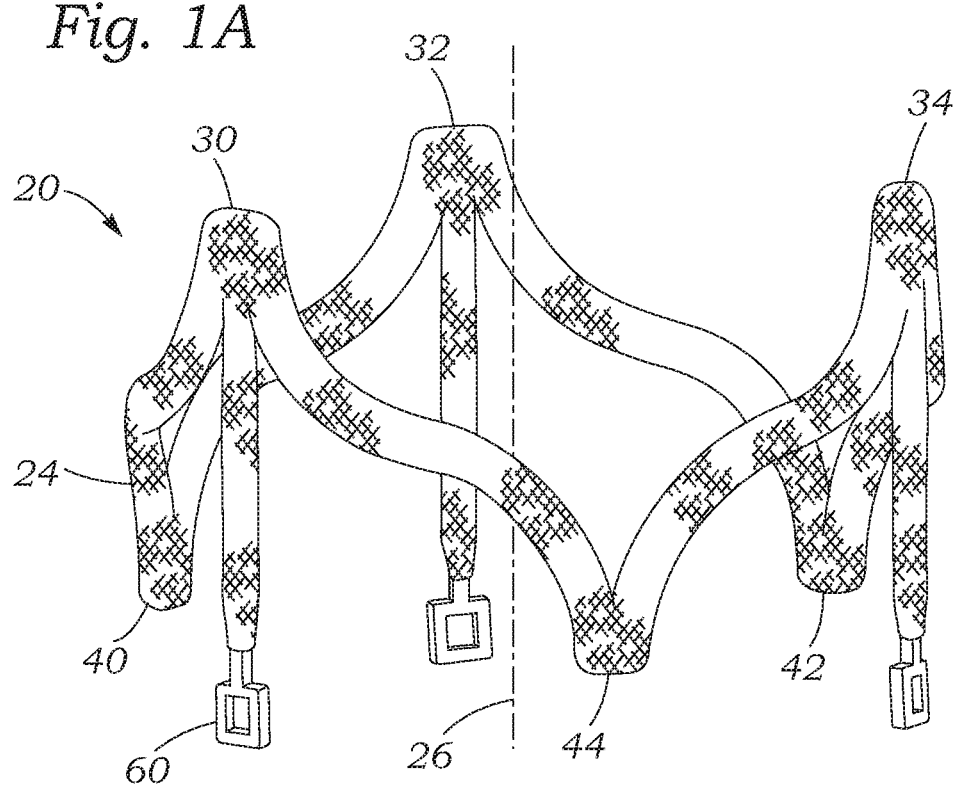
FIG. 1A is a perspective view of an exemplary fabric-covered pinch device (e.g., a grip, dock, constrictor, etc.) having three peaks and valleys around its circumference for use in heart valve placement procedures described herein.
Figure 1B:
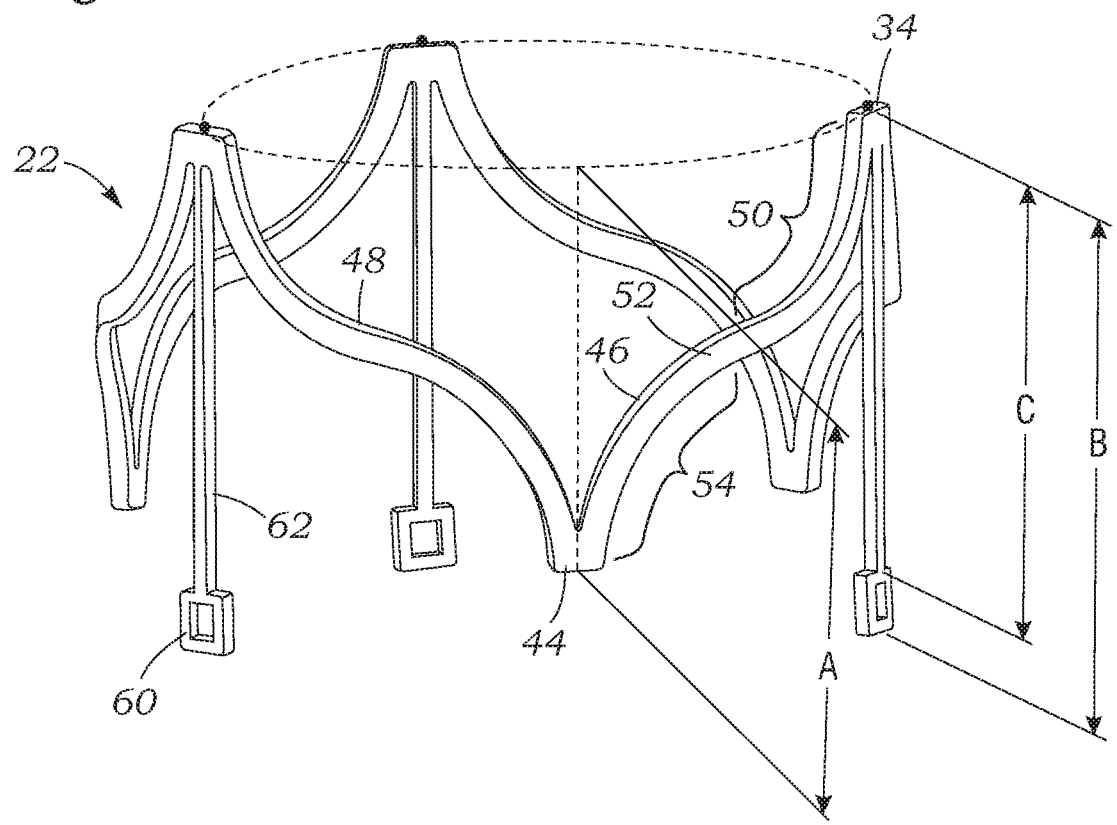
FIG. 1B is a perspective view of an inner body of the pinch device without the fabric covering.

FIG. 1A is a perspective view of an exemplary fabric-covered pinch device 20 (grip, dock, constrictor, etc.), and FIG. 1B is a perspective view of an inner body 22 of the pinch device without a fabric covering 24. The pinch device 20 has a generally annular or toroidal body arranged around a vertical Z-axis 26 and formed from a suitable super-elastic metal or alloy, such as Nitinol. Other shapes and/or materials are also possible. Optionally, spring steel, a cobalt-chrome alloy such as Elgiloy®, or other such elastic metals can be utilized with some modification to the delivery system. Desirably, the material from which the pinch device 20 is fabricated allows it to be radially compressed to a reduced profile for delivery through the patient's vasculature and automatically expanded to its functional size and shape when deployed. With a supra-elastic material such as Nitinol the reduced radial profile can be very small, whereas with other materials which are not so flexible, the pinch device 20 may only be partially constricted for delivery and then permitted to expand.

Although various numbers/arrangements of peaks and valleys are possible, the illustrated pinch device 20 includes three peaks 30, 32, 34 evenly alternating with three valleys 40, 42, 44 around its circumference. More particularly, the peaks 30, 32, 34 are spaced 120° apart, each 60° separated from adjacent valleys 40, 42, 44. The peaks and valleys desirably lie in a tubular space such that the peaks 30, 32, 34 are positioned above the valleys 40, 42, 44 in the Z-direction. In some embodiments, the peaks 30, 32, 34 have greater radii than the valleys 40, 42, 44, or vice versa. For instance, in some embodiments, the projection of the pinch device 20 onto an x-y plane forms a closed shape having a variable radius (e.g., a starfish shape).

In terms of orientation, the pinch devices herein can be delivered in a direction toward the target native heart valve with either the peaks or the valleys leading, which will determine the proximal and distal directions. That is, the leading end of an implant in a delivery procedure is termed the distal end, and vice versa. In the illustrated embodiment, the peaks 30, 32, 34 of the pinch device 20 are on the leading end and thus form the distal end of the device, while the valleys 40, 42, 44 are on the trailing or proximal end. Furthermore, for the purpose of clarity and reference, the distal direction coincides with up along the Z-axis 26 in FIGS. 1A and 1B, while the proximal direction coincides with down.

A plurality of struts can be used between adjacent peaks and/or valleys. For example, circumferential struts 46, 48 connect each two adjacent peaks 30, 32, 34 and valleys 40, 42, 44. More particularly, as viewed looking down along the axis 26, a first circumferential strut 46 extends clockwise (CW) down from each one of the peaks 30, 32, 34 to each one of the valleys 40, 42, 44, and a second circumferential strut 48 extends up from the valley CW to the next peak. The struts (e.g., circumferential struts 46, 48) can be configured in a variety of shapes and sizes, e.g., straight, curved, zig-zag, symmetrical, asymmetrical, etc. For example, in FIGS. 1A and 1B, the struts 46, 48 are shown as being generally S-shaped, with two distinct curvatures separated by a point of inflection. Each of the struts 46, 48 can terminate at its corresponding peak and valley in an asymptotic manner such that it is nearly aligned with the vertical Z-axis 26. Looking at the first circumferential strut 46 in FIGS. 1A and 1B extending between the peak 34 and the valley 44, a first segment 50 initially extends downward in a nearly vertical direction and has a concave up curvature until a point of inflection 52 at a midpoint of the strut. From there, a second segment 54 is curved concave down until it is nearly vertical at the valley 44. When implanted, the struts 46, 48 are in direct contact with the native heart valve leaflets, as will be explained, and this S-shaped configuration enhances their ability to pinch or clamp a wide area of the leaflet against the expandable heart valve that is positioned within the leaflets.

A plurality of buckles 60 (e.g., 2, 3, 4, 5, 6, or more) can be integrated with the inner body 22 to facilitate manipulation and deployment of the pinch device 20. The term "integrated" in this regard means that the buckles 60 are either formed homogeneously with the rest of the inner body 22 as a single piece, or that the buckles are secured to the inner body 22 in a manner which enables manipulation of the buckles to manipulate the inner body. For example, the buckles 60 may be welded to the inner body 22 after fabrication of both. Each buckle of the plurality of buckles 60 can be positioned on an end of an extension (e.g., a finger, peak, etc.). In the illustrated embodiment, each buckle 60 is positioned on the lower end of a vertical finger 62 projecting downward from each one of the peaks 30, 32, 34. As seen in FIG. 1A, each of the buckles 60 remains exposed by virtue of not being covered by the fabric 24, but embodiments in which the buckles 60 are covered are also possible. Not covering the buckles 60 may help prevent interference of the fabric covering with the release/deployment arms that hold the pinch device during delivery.

The extensions (e.g., fingers, etc.) can have a variety of shapes and sizes. For example, in FIGS. 1A and 1B, the vertical height A as measured along the Z-axis 26 between the peaks 30, 32, 34 and valleys 40, 42, 44 is shorter than the length B of each finger 62 with buckle 60, such that the buckles 60 extend below the valleys 40, 42, 44. In one embodiment, the height A can be between 13-14 mm, preferably about 13.9 mm, and the length B of each finger 62 with buckle 60 can be between 16-18 mm, and preferably about 17.0 mm. Each one of the illustrated buckles 60 can have a substantially open square shape, although other configurations/shapes (e.g., circular, oval, rectangular, polygonal, etc.) are contemplated. Each buckle 60 can have a height of about 2 mm, such that the height C of each finger 62 is between about 14-16 mm, and preferably about 15.0 mm. A circumferential span between each two adjacent peaks 30, 32, 34 (or between each two adjacent valleys 40, 42, 44) can vary depending on the particular size of valve being implanted, for example between about 23-29 mm. In one embodiment, the circumferential span between each two adjacent peaks 30, 32, 34 is about 27.1 mm such that a diameter of the inner body 22 when formed into a toroid is about 25.9 mm, which would be suitable for clamping around a heart valve that expands to 27 mm.

The size of the pinch device 20 can vary from implementation to implementation. In particular embodiments, the pinch device 20 can be sized such that the pinch device can be positioned within the aorta of a patient at a location adjacent to the aortic valve, circumscribing the aortic valve and its leaflets. In order to frictionally secure a prosthetic heart valve in its interior, the pinch device 20 has an expanded diameter that is slightly smaller than the diameter of the prosthetic heart valve when fully expanded. In particular embodiments, for instance, the pinch device can have an inner or outer diameter between 10 and 50 mm (e.g., between 17 and 28 mm) and a height between 5 and 35 mm (e.g., between 8 and 18 mm). Furthermore, the thickness of the annular body of the pinch device 20 may vary from embodiment to embodiment, but in certain embodiments is between 0.3 and 1.2 mm. The pinch device 20 can be formed by laser-cutting the shape from a tubular blank, resulting in square or rectangular cross-sectional struts. Subsequently, the struts may be further processed such as with electropolishing to reduce any sharp edges or corners. Other manufacturing and processing techniques are also possible.

As seen best in FIG. 1B, the peaks 30, 32, 34 and valleys 40, 42, 44 can have flat ends that are perpendicular to the Z-axis 26. This feature facilitates laser fabrication of the pinch device 20 by eliminating tight curvatures at these points. Furthermore, because the peaks 30, 32, 34 comprise the leading end during a transapical delivery, these flat ends help prevent puncture of anatomical structures in case of any contact therewith.

Delivery Method

FIGS. 2A-2E are schematic sectional views of a native aortic valve AV showing sequential steps in an exemplary deployment of an exemplary pinch device 20 and an expandable prosthetic heart valve therein during a beating heart valve replacement procedure. As mentioned, the exemplary procedure is one which utilizes a transapical access route to replace a dysfunctional aortic valve. The presently disclosed pinch device 20 and associated delivery system are designed for this access route and native valve replacement, but those of skill in art will understand that certain modifications will enable procedures utilizing alternative access routes and for replacing different native valves. For example, the same transapical access route may be used to replace a mitral valve MV, though the shape of the pinch device 20 may be modified to negotiate the chordae tendineae below the mitral valve.

Figure 2A:
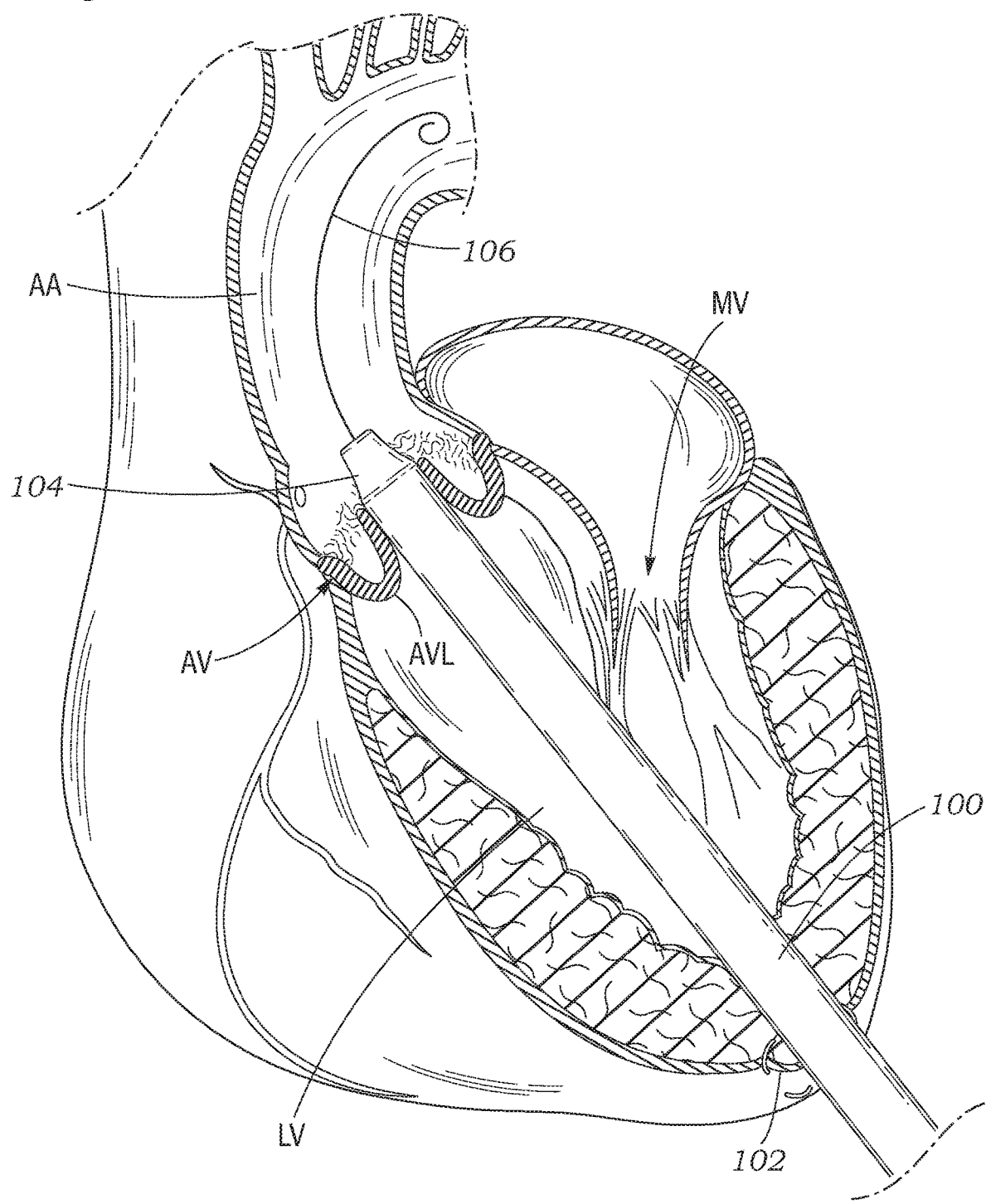
FIGS. 2A-2E are schematic sectional views of a native aortic valve showing sequential steps in transapical deployment of the exemplary pinch device and an expandable prosthetic heart valve therein during an aortic valve replacement procedure.

In any event, the exemplary procedure commences by introduction of an access or delivery sheath 100 of an access or delivery system into the left ventricle LV through an apical puncture 102 and advancing a distal end 104 of the sheath along a previously located/positioned guide wire 106 into proximity with the aortic valve AV. Although, use of a guidewire is optional. As seen in FIG. 2A, the distal end 104 can be positioned slightly beyond the aortic valve leaflets AVL and into the ascending aorta AA. Positioning of the distal end 104 can be assisted by external visualization such as ultrasound and/or fluoroscopy and radiopaque markers in the distal end.

Because the apical puncture 102 is properly sealed around the access/delivery sheath 100, and due to other surgical precautions, the operation can be accomplished while the heart is beating. Although not shown, introduction of the access/delivery sheath 100 to the apical puncture 102 typically occurs via an intercostal incision, often termed a "mini-thoracotomy." Local exposure of the exterior of the heart is then attained using subcutaneous incisions along with tissue spreaders and the like. The apical puncture 102 itself is initially formed using a small needle, and the puncture thereby formed is enlarged using a dilator. Purse string sutures or an access valve can be installed at the left ventricular apex so that the access or delivery sheath 100 may be advanced into the left ventricle without significant loss of blood.

Figure 2B:
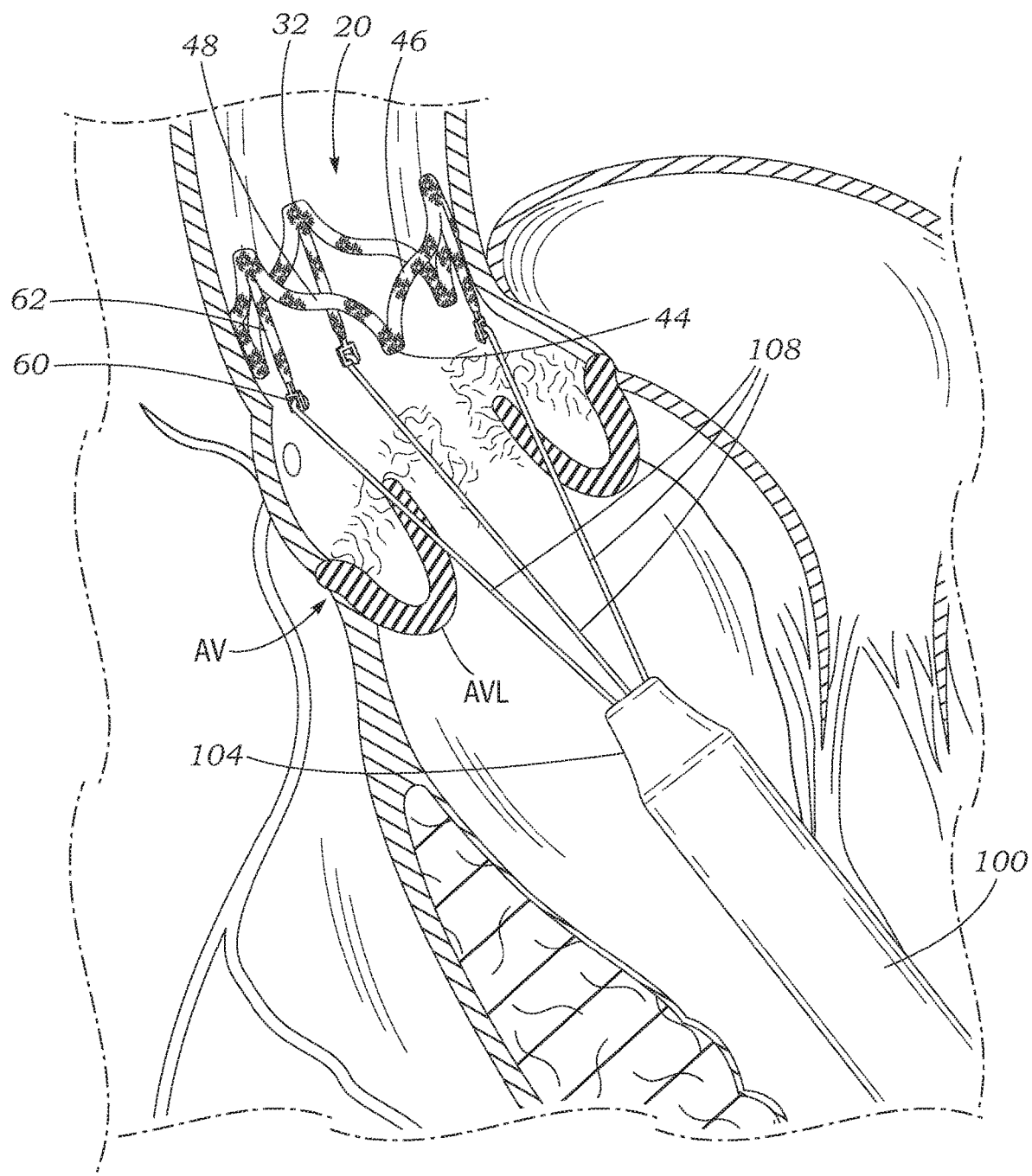

FIG. 2B illustrates the procedure after expulsion of the pinch device 20 from the access/delivery sheath 100 into the ascending aorta, and/or retraction of the distal end 104 of the sheath into the left ventricle. The health care provider (e.g., doctor, surgeon, etc.) can maintain control of position of the pinch device 20 during this retraction, e.g., by virtue of a plurality of deployment arms 108 that engage the buckles 60. The deployment arms 108 can be fixed or can be slidable within the access/delivery sheath 100 and thus permit axial movement of the pinch device 20. Furthermore, the deployment arms 108 can have sufficient stiffness to permit the health care provider (e.g., doctor, surgeon, etc.) to translate rotational movement of the access sheath 100 to rotation of the pinch device 20.

The illustrated pinch device 20 has three buckles 60 and thus three deployment arms 108. Additional details of the control mechanism for deploying the pinch device 20 will be described below. At this stage, the pinch device 20 has fully self-expanded and is positioned above the aortic valve AV. The arms 108 can extend across a native valve at the commissures such that the arms and pinch device allow the native leaflets to continue functioning during deployment. For example, although not shown in the two-dimensional depiction, the three deployment arms 108 extend across the aortic valve AV at the commissures between the aortic valve leaflets AVL. In this way, the deployment arms 108 do not interfere with proper functioning of the leaflets, enabling the heart to continue to pump blood. Similar effect can be accomplished at the mitral valve using, for example, two arms 108 that connect to two buckles and cross at the two commissures of the mitral valve. Modifications for other valves are also possible.

The buckle 60 and vertical finger 62 can align with each of the peaks (e.g., the three peaks 30, 32, 34) of the pinch device 20. Therefore, the peaks (e.g., the three peaks 30, 32, 34) can align with the native heart valve commissures, and the valleys (e.g., the three valleys 40, 42, 46) and any intermediate struts (e.g., 46, 48) can align with the native valve leaflets (e.g., the three aortic valve leaflets AVL). Again, proper axial and rotational positioning of the pinch device 20 can be accomplished by manipulation of the deployment arms 108 and/or access sheath 100, and can be facilitated by radiopaque markers on the pinch device 20 or deployment arms 108 that can be imaged from outside the body.

Figure 2C:
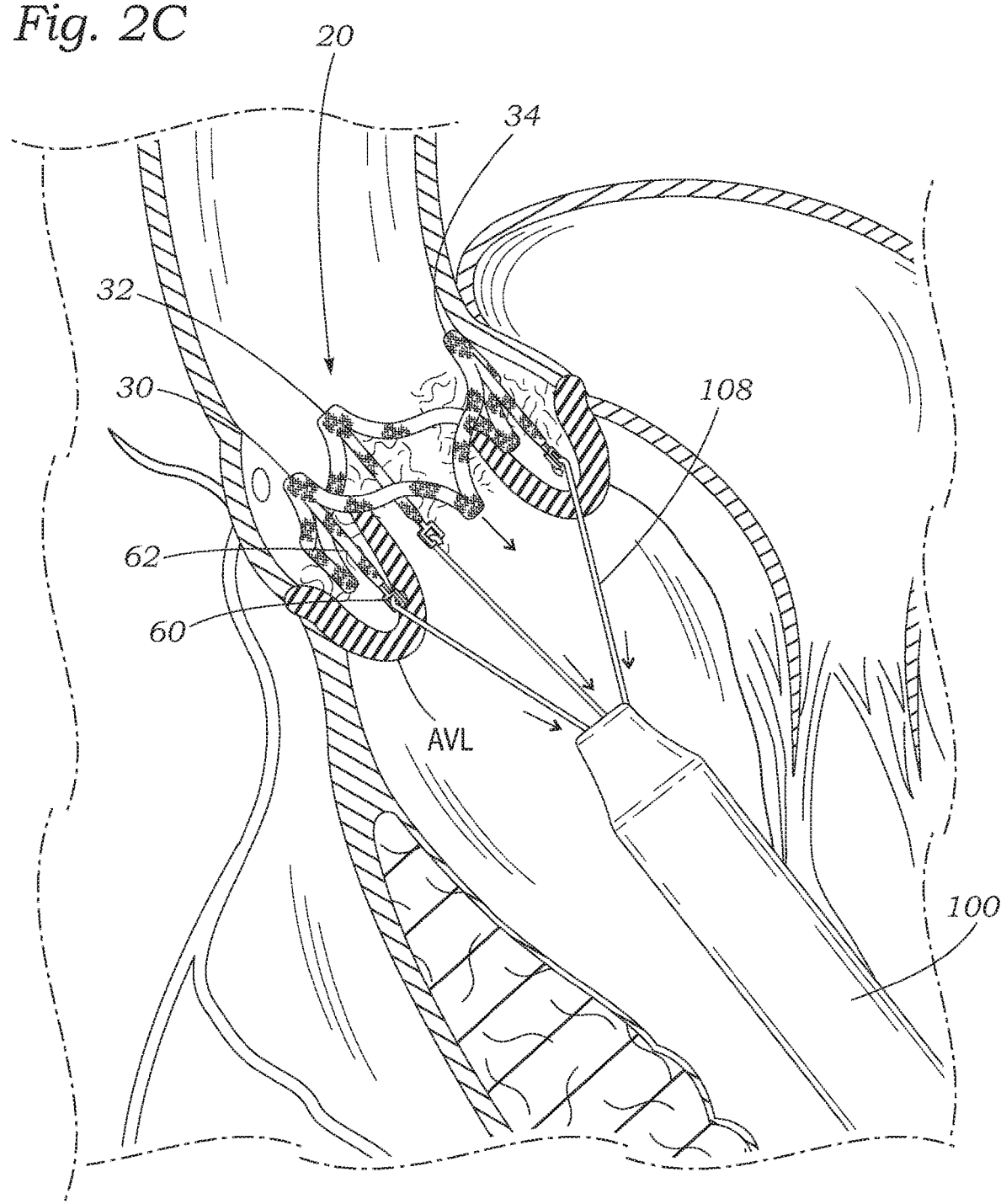

FIG. 2C shows the pinch device 20 is moved from the location where it was expanded to a location closer to or in contact with the native valve (e.g., with the struts/peaks/valleys generally positioned outside or encircling the native leaflets). For example, in the example shown, the pinch device 20 is retracted proximally until it is generally positioned at the aortic valve AV to the outside of the aortic valve leaflets AVL. Again, although it is not shown in two dimensions, the circumferential span of the pinch device 20 between the peaks 30, 32, 34 (comprising the struts 46, 48 and one of the valleys 40, 42, 44) lies to the outside of each of the three aortic valve leaflets AVL. Conversely, the peaks 30, 32, 34 as well as the vertical struts 62 are aligned with the aortic valve commissures and pass between the aortic valve leaflets AVL. The buckles 60 and terminal end of the deployment arms 108 can be located above or below the level of the native valve or aortic valve AV, depending on the precise positioning and length of the vertical struts 62. Retraction of the pinch device 20 may be accomplished by retracting the deployment arms 108 into the access sheath 100, as shown, or simply by pulling back the access sheath 100 in a proximal direction.

Figure 2D:
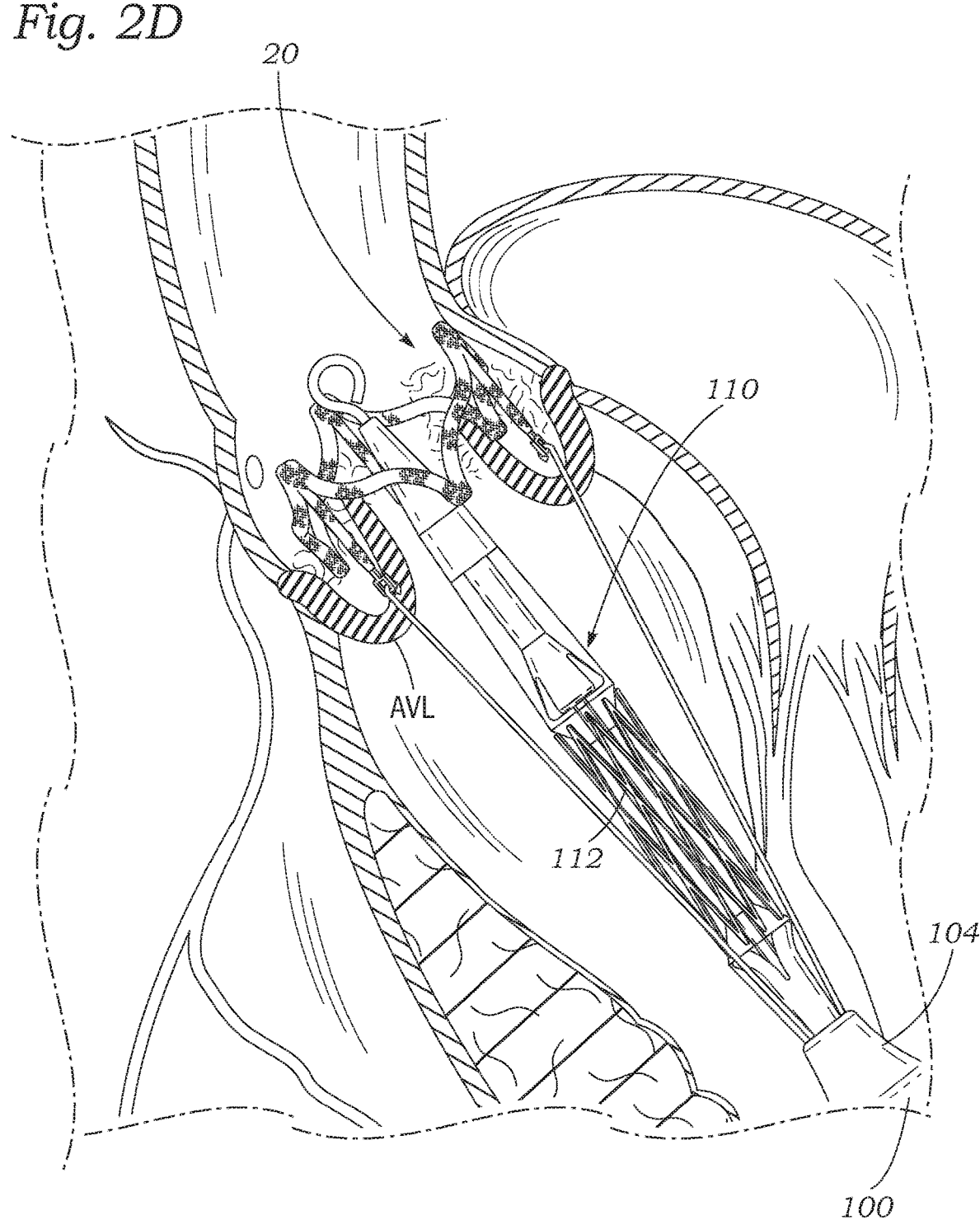

In FIG. 2D, a delivery catheter 110 having a prosthetic heart valve 112 mounted thereon has been advanced through the access sheath 100 until the heart valve is expelled from the distal end 104. The access sheath 100 has an internal lumen (not shown) sufficiently large to enable passage of the delivery catheter 110 therethrough even in the presence of the deployment arms 108. The delivery catheter 110 can be one used for delivering a variety of expandable heart valves 112, such as for example the Edwards Certitude Delivery System from Edwards Lifesciences of Irvine, Calif. which is used to transapically deliver the SAPIEN 3 Transcatheter Heart Valve. The Certitude Delivery System is designed for use through lumens of access sheaths having an outer dimension of 18 Fr, which is equivalent to a diameter of 6 mm. Other delivery catheters and configurations are also possible as the access/delivery sheath 100 can be configured to allow different types of delivery catheters to be introduced or passed therethrough.

Figure 2E:
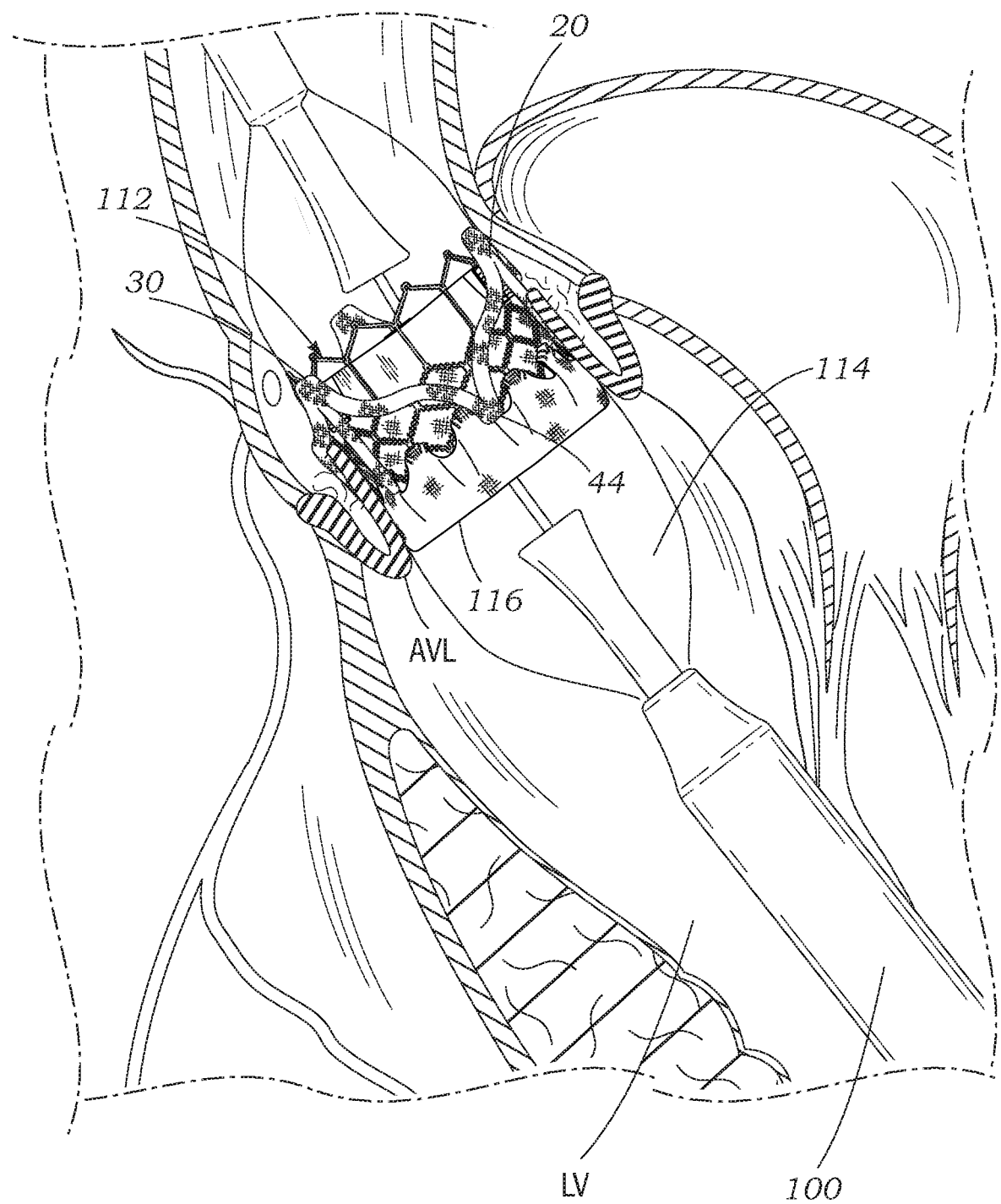

FIG. 2E subsequently shows advancement of the prosthetic heart valve 112 into a position within the native valve and pinch device and outward expansion of the prosthetic heart valve. For example, FIG. 2E shows advancement of the prosthetic heart valve 112 into a position within the aortic valve leaflets AVL and outward expansion thereof. In the illustrated embodiment, a balloon 114 on the distal end of the balloon catheter 110 is used to plastically expand the heart valve 112 outward into contact with the leaflets. Due to the surrounding presence of the pinch device 20, the leaflets are clamped or pinched (e.g., partially or fully) therebetween. Typically, the expanded diameter of the pinch device 20 is slightly smaller than the fully expanded diameter of the heart valve 112. In this manner, full expansion of the heart valve 112 causes slight outward expansion of the pinch device 20, which sets up a reactive inward resilient spring force. Preferably, the diameters of the fully expanded heart valve 112 and fully expanded pinch device 20 are calibrated such that a predetermined clamping force is applied to the aortic valve leaflets AVL. For example, a clamping force of between about 1-3 pounds is considered desirable. This clamping force is sufficient to anchor the prosthetic heart valve 112 into place, resisting subsequent migration. Other forms of expansion of the heart valve 112 are also possible, such as self-expansion, mechanical expansion, or a combination of expansion forms.

In terms of positioning, the heart valve 112 typically has three flexible leaflets (e.g., three artificial leaflets, leaflets formed of tissue such as pericardial tissue, etc.) therein divided by commissure regions. The three leaflets of the prosthetic valve 112 are thus aligned with the three native aortic valve leaflets AVL and thus with the portions of the pinch device 20 between the peaks 30, 32, 34. In a preferred embodiment, the heart valve 112 is longer axially than the axial dimension of the pinch device 20, at least between the peaks and valleys. The location of the distal end of the heart valve 112 is approximately the same as the peaks 30, 32, 34 of the pinch device 20, but the proximal end 116 is preferably located farther into the left ventricle LV than the valleys 40, 42, 44.

In one embodiment, the deployment arms 108 remain attached to the buckles 60 until a desired position of the heart valve 112 is established. For a balloon-expandable heart valve, once the balloon 114 is inflated, the support frame of the heart valve 112 expands outward into its final diameter, at which point the deployment arms 108 can be decoupled from the buckles 60. If the heart valve 112 is self-expandable, the health care provider (e.g., doctor, surgeon, etc.) can be able to first expand and then constrict the valve for repositioning if necessary. Alternatively, the deployment arms 108 may be decoupled from the buckles 60 prior to introduction of the heart valve 112, as seen in FIG. 2E. Again, radiopaque markers on the pinch device 20 and the heart valve 112 can be used to coordinate their dual deployment. It is important to note again that because of the single delivery system the heart valve 112 is initially concentric with the pinch device 20 such that just axial and rotational alignment is required.

FIG. 2E shows the heart valve 112 fully expanded which pinches the aortic valve leaflets AVL against the inward spring force of the pinch device 20. Because the cross-section is offset from the 120° spacing of the leaflets, this is not shown precisely in the drawing. During the process, the heart continues to beat and as soon as the heart valve 112 is expanded and the balloon 114 deflated, the prosthetic valve takes over the function of the native heart valve. Fluoroscopy can be used to confirm proper performance of the heart valve 112. Finally, the health care provider (e.g., doctor, surgeon, etc.) can retract the delivery catheter 110 with the deflated balloon 114 back into the access sheath 100. The entire delivery system is then removed from the body with the various puncture and access incisions closed up.

Additional Pinch Device Features and Configurations

Figure 3A:
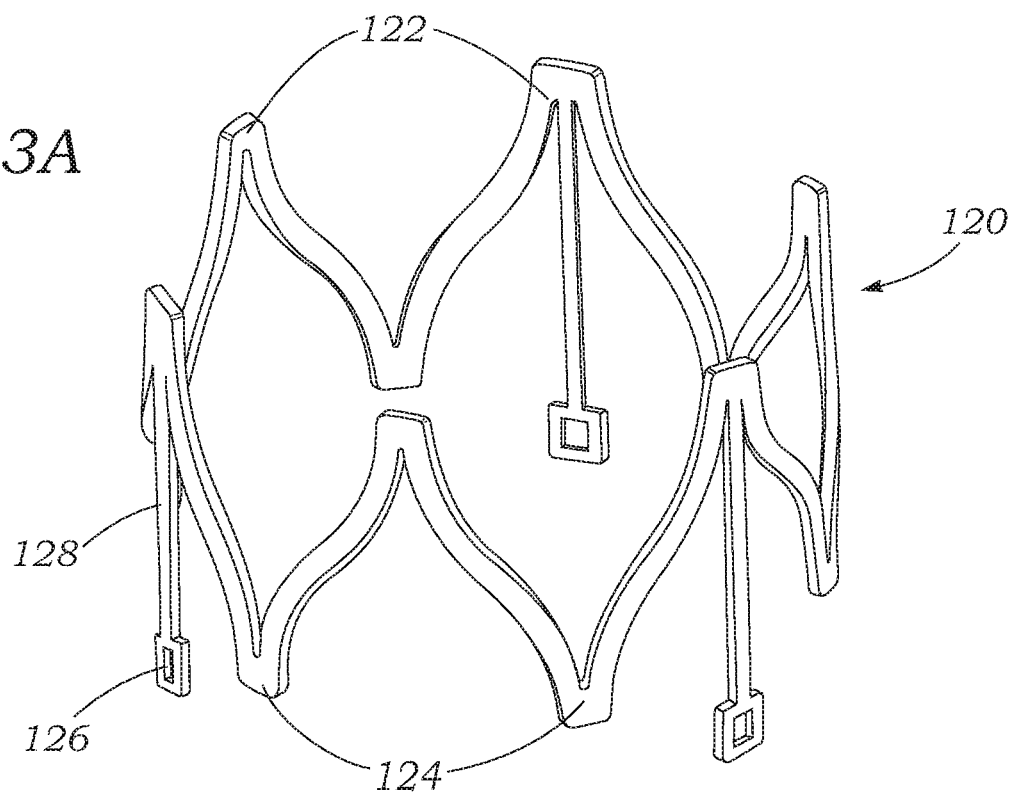
FIG. 3A is a perspective view of an exemplary pinch device having six peaks and valleys around its circumference for use in heart valve replacement procedures described herein.

Different numbers of peaks, valleys, struts, etc. can be used in a pinch device. For example, FIG. 3A is a perspective view of an exemplary pinch device 120 having six peaks 122 and six valleys 124 around its circumference for use in heart valve replacement procedures described herein. As above, there are buckles each at an end of an extension. For example, three buckles 126 at the lower end of three vertical extensions 128 (e.g., fingers or struts). The buckles 126 are positioned below every other peak 122, and thus the pinch device 120 is suitable for use at the aortic valve with the vertical struts 128 and buckles 126 extending along the commissures and between the leaflets thereof to allow function of the native leaflets during delivery and deployment. In between each of the peaks 122 having the integrated buckles 126, additional struts (shown in a W-shaped strut configuration) are provided which can enhance the clamping force of the pinch device 120 against the native leaflets.

Figure 3B:
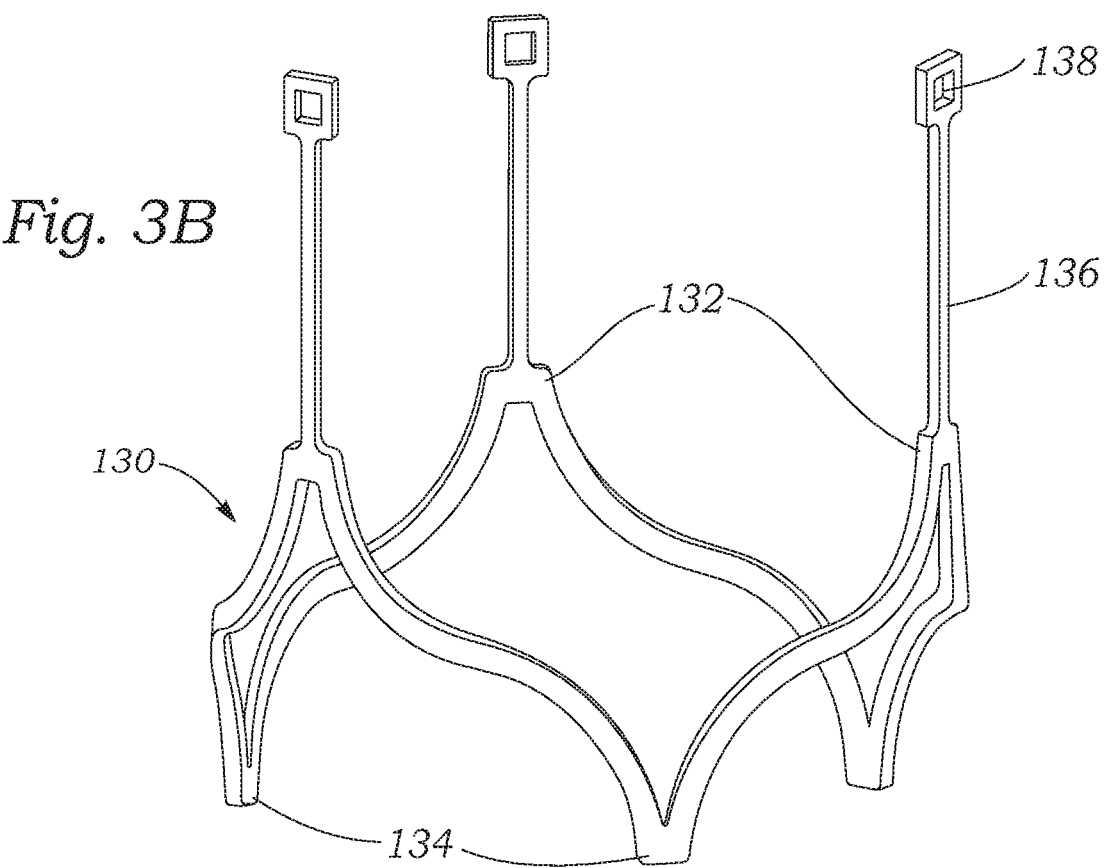
FIG. 3B is an exemplary pinch device modified for another valve replacement procedure.

The extensions and buckles can also be configured in different ways. For example, FIG. 3B is an exemplary pinch device 130 modified for an alternative valve replacement procedure. The main portion of the pinch device 130 is similar to the pinch device 20 described above, with three peaks 132 evenly spaced between three valleys 134. However, instead of the buckles extending downward from the peaks 132, extensions or vertical struts 136 having buckles 138 on their ends extend upward from the three peaks 132. With this configuration, the delivery system engages the pinch device 130 from above, meaning the peaks 132 are on the proximal end and the valleys 134 extend distally, in terms of delivery orientation. An exemplary procedure may involve advancing the delivery system through the vasculature and down the ascending aorta AA to deliver the pinch device 130 around the aortic valve leaflets AVL. Alternatively, the pinch device 130 may be advanced into a position around the mitral valve leaflets. It will be understood that a number of possible delivery routes and valve replacement procedures may be performed using the pinch device 130.

Access/Delivery System

FIGS. 4A-4D are perspective views of an exemplary access or delivery system 150 having the tubular access or delivery sheath 100 described above showing sequential steps in expulsion and release of the pinch device 20 from the sheath. The access system 150 includes the access sheath 100 extending distally from a proximal handle 152, and can include and/or house a linear displacement mechanism for the pinch device 20 and/or sheath. For example, the displacement mechanism can be configured to move the sheath relative to the pinch device and handle (e.g., the pinch device and the handle or a portion of the handle can be fixed relative to each other, while the sheath moves), can be configured to move the pinch device relative to the sheath and handle (e.g., the sheath and handle or a portion of the handle can be fixed relative to each other, while the pinch device moves), a combination of these, etc. In the illustrated embodiment, the handle 152 includes a proximal grip portion 154 slidably mounted over a distal housing 156 in a telescoping fashion. The grip portion 154 is fixed to move linearly with respect to the deployment arms 108 which in turn are coupled to the buckles 60 (FIG. 2B) on the pinch device 20. The grip portion 154 is shown moving to the left between FIGS. 4A and 4B relative to the housing 156 which expels the pinch device 20 from the distal end 104 of the access sheath 100.

Linear motion of the grip portion 154 relative to the housing 156 may be accomplished in a variety of ways. In the illustrations, a thumbwheel 160 having gear teeth on its periphery is mounted for rotation on the grip portion 154 and has a lower generatrix in meshing engagement with a rack 162 having similar gear teeth axially positioned on the housing 156. A user can easily hold the grip portion 154 while manipulating the thumbwheel 160 to expel the pinch device 20 from the sheath 100. Alternatively, the handle 152 may be formed of a single member incorporating a linear slider which may be moved back and forth to displace the pinch device 20. Still further linear displacement mechanisms or other displacement mechanisms are contemplated.

Figure 4A:
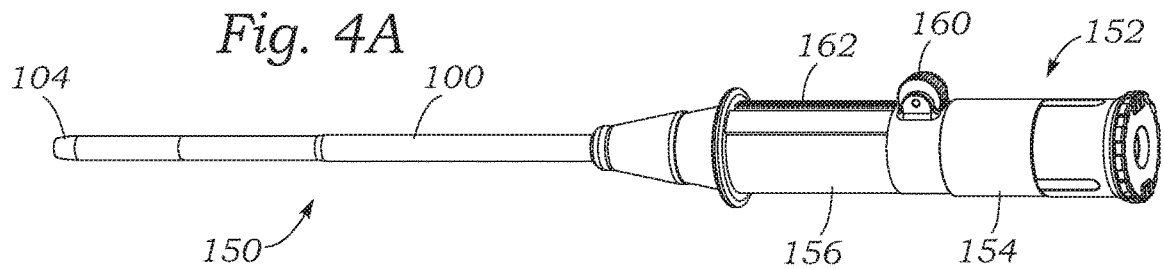
FIGS. 4A-4D are perspective views of an exemplary access/delivery system having a tubular access/delivery sheath for deploying the pinch devices described herein showing sequential steps in expulsion and release of an exemplary pinch device from the sheath.
Figure 4B:
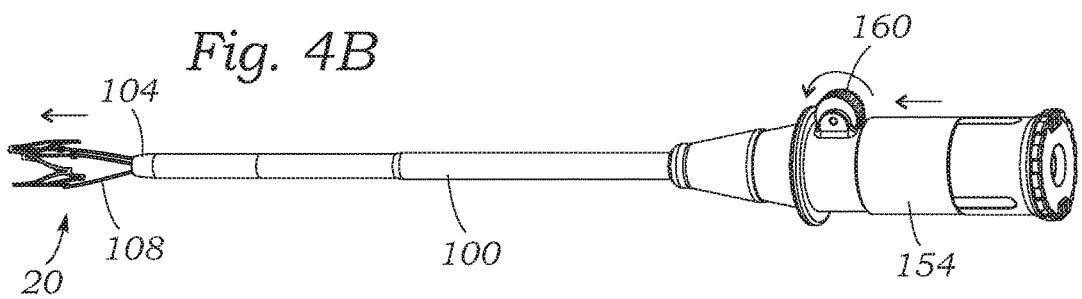
Figure 4C:
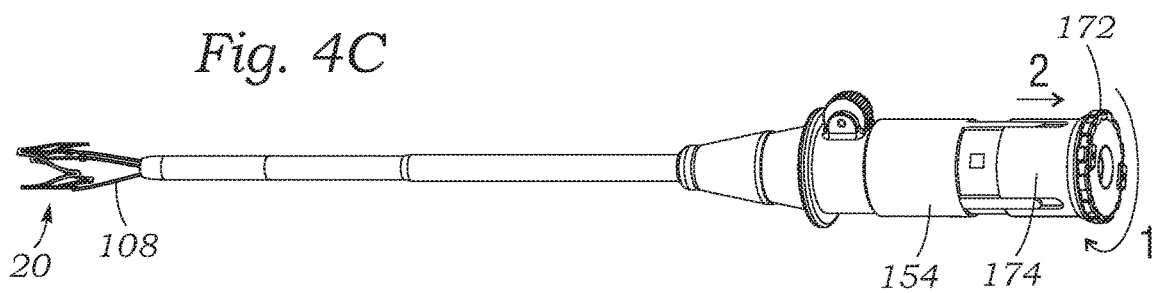
Figures 5A, 5B:
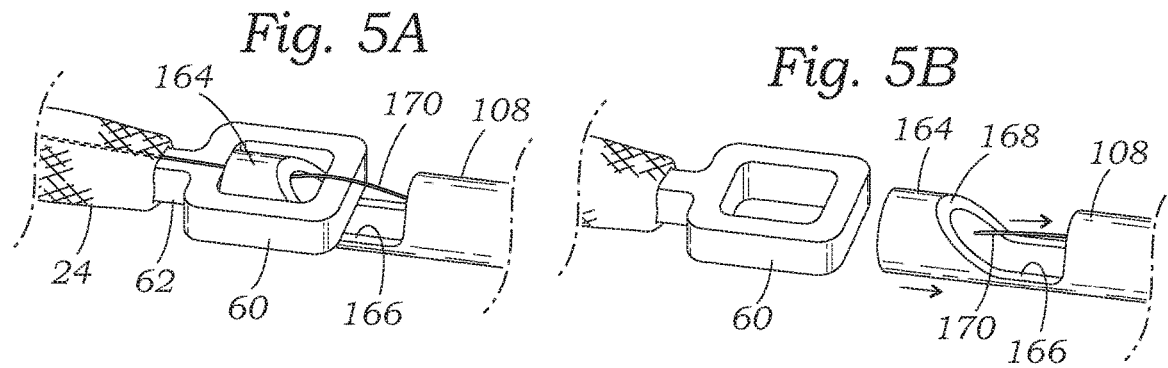
FIGS. 5A and 5B are enlarged perspective views of an exemplary coupling arrangement between one of a plurality of deployment arms extending from the access sheath and an exemplary manipulation buckle extending proximally from the pinch device in both coupled and uncoupled configurations.
Figure 4D:
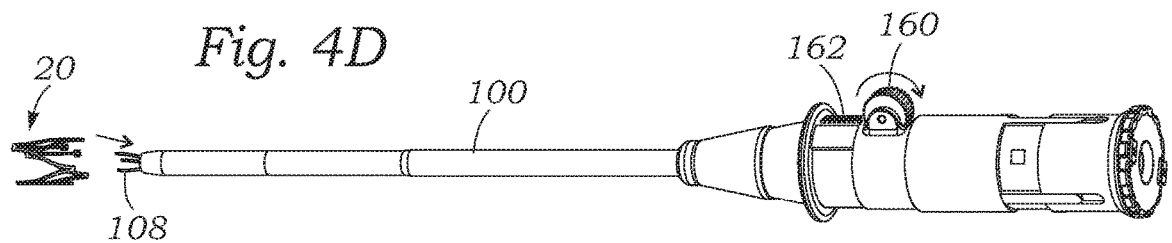

FIGS. 4C and 4D, in conjunction with FIGS. 5A and 5B, show an exemplary configuration for coupling and decoupling the deployment arms 108 and the buckles 60 on the pinch device 20, although other configurations are also possible. In the enlarged view of FIG. 5A, a distal end 164 of one of the deployment arms 108 extends within the central aperture of the open square buckle 60. The deployment arms 108 are tubular and the distal end 164 is separated from the main portion of the arm by a cutout 166 formed partly as a ramped edge 168 on its distal side. A filament 170 extends along the length of the tubular arm 108, emerges at the cutout 166, and passes over a proximal portion of the buckle 60 and through the distal end 164. The filament 170 then continues in a distal direction along the vertical strut 62 and can be tucked underneath the fabric 24 that covers the pinch device 20. The filament 170 can be made of a polymer suture material, can be a thin Nitinol wire, or be made of another suitable material. By this arrangement, the buckle 60 is captured within the cutout 166 at the distal end of the deployment arm 108.

FIG. 5B is an enlarged view of the deployment arm 108 decoupling from the buckle 60. In particular, the filament 170 is retracted proximally which releases the buckle 60 from within the cutout 166. The ramped edge 168 facilitates the release by minimizing any friction.

The filament 170 can be retracted in a variety of ways. For example, FIG. 4C illustrates an exemplary two-step operation for retracting the filament 170, which is also shown in greater detail in FIGS. 7A-7C. Namely, in step 1 the user first rotates an end cap 172 provided on a proximal end of the handle 152 which enables proximal movement of an end sleeve 174 in step 2. As will be described below with reference to FIG. 6E, the filament 170 is fixed linearly with respect to the end sleeve 174 and moves relative to the deployment arm 108 with the end sleeve. Of course, all three filaments 170 are displaced in a proximal direction with the end sleeve 174, which releases all three buckles 60 and decouples the access system 150 from the pinch device 20.

FIG. 4D illustrates subsequent proximal retraction of the deployment arms 108 within the access sheath 100. This can be accomplished by reversing the direction of the thumbwheel 160 on the rack 162 which can pull the grip portion 154 back along the housing 156. As mentioned above, this operation can be performed prior to or after advancement of the prosthetic heart valve delivery catheter 110.

Figure 6C:
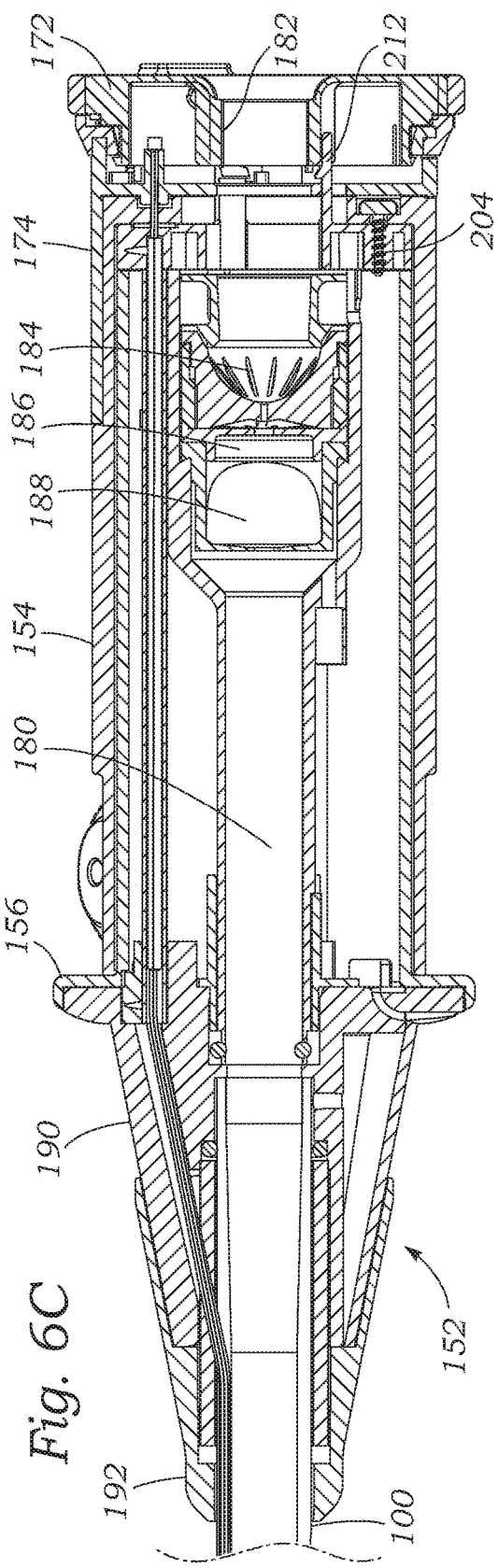
FIG. 6C is a vertical sectional view through the proximal handle of the access system in particular showing a number of exemplary hemostatic seals.
Figure 6E:
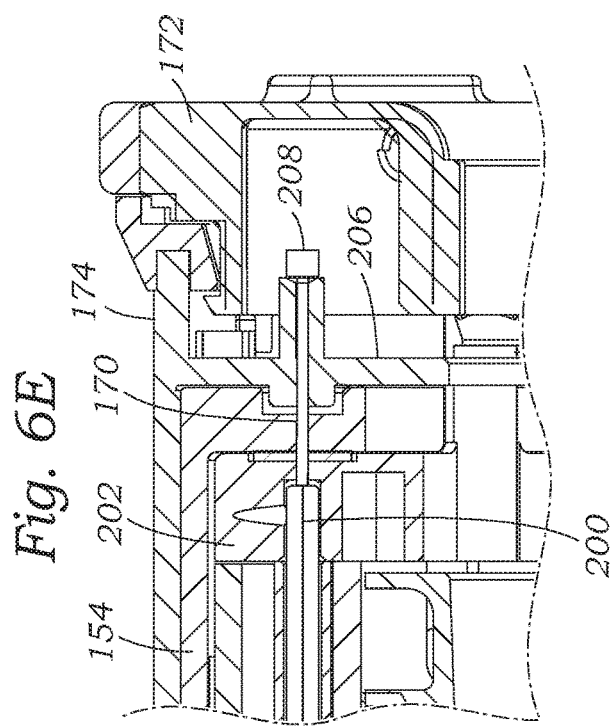
FIGS. 6D and 6E are enlarged views of portions thereof.
Figure 6D:
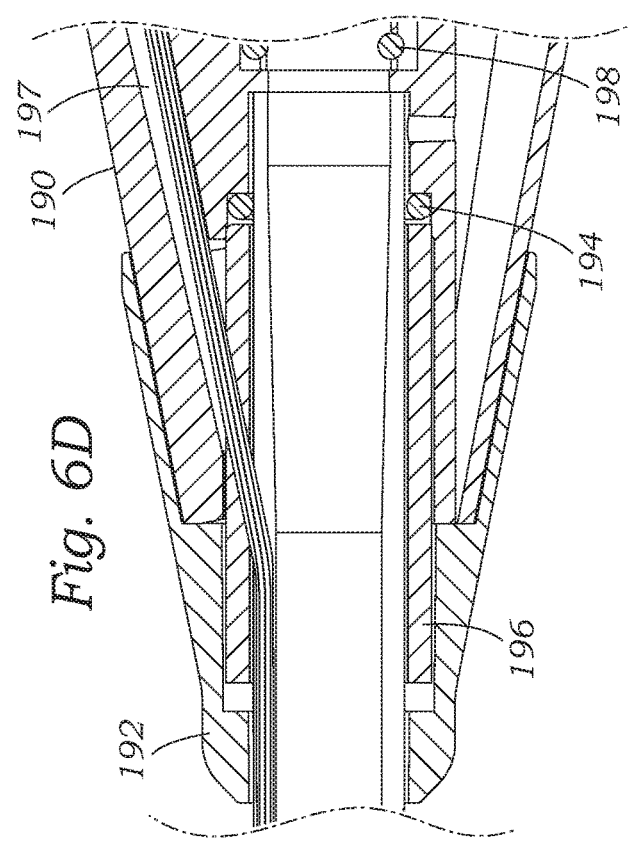

FIG. 6A is a broken vertical sectional view through the exemplary access system 150 including the access sheath 100 with a pinch device 20 compressed and held therein. FIG. 6B is a vertical sectional view through a distal end of the access sheath 100 after expulsion of the pinch device 20 therefrom but before decoupling of the deployment arms 108. FIG. 6C is a sectional view through the proximal handle 152 in particular showing a number of hemostatic seals, while FIGS. 6D and 6E are enlarged views of portions of FIG. 6C.

The access/delivery sheath 100 can be inserted into a body and extend into the heart from the exterior of the body, with the proximal handle 152 located outside the body. In one embodiment, the access sheath 100 possesses an external hydrophilic coating and has a length of at least 8 inches (~20 cm) so that it can extend from outside the body into the left ventricle and reach the native annulus or aortic annulus. However, for transapical procedures, the access sheath 100 can have a maximum length of about 12 inches (~30 cm) to avoid becoming unduly flexible.

The handle 152 in FIG. 6A is in the same configuration as seen in solid line in FIG. 4A, with the grip portion 154 telescoped proximally away from the housing 156. Consequently, the deployment arms 108 and pinch device 20 are retracted into the access sheath 100. Once deployed, as seen in FIG. 6B, the deployment arms 108 can project forward from or relative to the distal end 104 of the sheath. The natural elasticity (or, optionally, pre-set shape, e.g. in shape memory material) of the pinch device 20 can permit it to expand to an enlarged diameter. Because of the high flexibility of the deployment arms 108, they can flex outwardly by virtue of their engagement with the buckles 60.

It should be noted that when the pinch device 20 is retracted within the access sheath 100, a central channel remains through the pinch device even though it is compressed into a much smaller diameter. The central channel permits passage of a guide wire, such as that shown at 106 in FIG. 2A, or other instruments used during the insertion procedure. It should also be noted that, when the pinch device 20 is constricted into its smaller diameter within the sheath 100, the V-shaped struts 46, 48 can come together in linear alignment and extend, such that the valleys 40, 42, 44 are located proximal to the buckles 60. Conversely, when expanded, the struts (e.g., V-shaped struts 46, 48) can spread apart and be shorter axially, and the buckles 60 can be located proximal thereto as shown in FIG. 6B.

The handle 152 provides both a mechanism for displacing the pinch device 20 axially as well as a number of seals for preventing blood leakage around instruments passed therethrough, including the heart valve delivery catheter 110. In this regard, the access system 150 functions somewhat like an introducer used to establish an access pathway into the heart for passage of instruments. For example, as seen in FIG. 6C, a central lumen 180 can extend through the middle of the handle 152 from the proximal end of the access sheath 100 to an aperture 182 in the end cap 172. The central lumen 180 in the handle 152 can be common with and extend into the lumen within the access sheath 104 for passage of the delivery catheter 110 (e.g., a balloon catheter, etc.). Within the handle lumen 180 can reside one or more valves, for example, hemostasis valves 184, 186, 188, which can be mounted within an inner housing or funnel-shaped inner housing for sealing around different sized instruments. For example, looking in series from proximal to distal in FIG. 6C, the handle 152 encompasses a cross-slit valve 184, a disk valve 186, and a duck-bill valve 188. These three valves function to provide a seal when there are no instruments, as well as when several different sizes of instruments pass through the handle 152. For example, the valves can seal around both the guidewire 106 and the delivery catheter 110 as previously shown.

Additionally, the access/delivery system can include one or more seals between parts of the handle 152 that prevent leakage from within the central lumen 180. The housing 156 can be attached to a tapered distal nose 190 around the distal end of which can be provided an elastomeric stress relief ferrule 192. The proximal end of the access sheath 100 can be fitted closely through a through bore in the ferrule 192 and can be secured within a lumen of the distal nose 190. As seen best in FIG. 6D, an O-ring 194 can be used to provide a seal around the exterior of the access sheath 100 and the interior of the distal nose 190. Furthermore, a tubular elastomeric seal 196 can be used and can be configured such that it extend around a segment of the access sheath 100 that spans the junction between the distal nose 190 and ferrule 192. Each of the deployment arms 108 can extend proximally into the handle from channels within the access sheath 100 and can angle radially outward into channels 197 in the distal nose 190. In doing so, the deployment arms 108 pass outward through the wall of the access sheath 100. To prevent blood leakage through these openings, the arms 108 can pass through small apertures that can be formed in the elastomeric seal 196, which apertures can be configured to close/seal around each of the deployment arms 108 and prevent leakage. At the same time, the apertures in the seal 196 can be configured and formed such that they do not unduly inhibit sliding movement of the deployment arms 108 therethrough. A second O-ring 198 can be used to further provide a seal around a distal end of the inner housing. In this way, blood that travels proximally through the access sheath 100 is prevented from escaping radially outward through the central lumen 180 within the handle 152.

FIG. 6E illustrates a proximal section of the handle 152 which is instructive in understanding the exemplary mechanism shown for decoupling the deployment arms 108 from the pinch device 20. As mentioned above, the grip portion 154 slidably mounts over the distal housing 156 in a telescoping fashion. A proximal end 200 of each deployment arm 108 is secured within a bore of an annular washer 202 that is secured within the grip portion 154 such as with fasteners 204 (see FIG. 6C). Consequently, the deployment arms 108 are secured to and move axially with the grip portion 154. The inner filaments 170 that extend through the deployment arms 108 continue proximally through an aperture formed in the proximal end of the grip portion 154 and through another aperture provided in an annular wall 206 which is part of the end sleeve 174. An enlargement 208 such as a crimped tube, bead, or other such device is secured to a proximal end of the filament 170 to prevent the filament from being able to slide distally relative to the end sleeve 174. Consequently, when the end sleeve 174 is displaced in a proximal direction relative to the grip portion 154, such as was described above with reference to FIG. 4C, the filament 170 is also displaced in proximal direction relative to the respective deployment arm 108.

FIGS. 7A-7C are enlarged views of the proximal end of the access system handle 152 showing operation of the exemplary decoupling assembly for the deployment arms 108. FIG. 7A illustrates inward compression of a pair of spring-loaded locking buttons 210 to permit rotation of the end cap 172. More specifically, the locking buttons 210 can be configured to prevent rotation of the end cap 172 until they are depressed. Other locking mechanisms to prevent undesired rotation are also possible. As described above, the end cap 172 is rotated in a clockwise (CW) direction prior to displacing the end sleeve 174 proximally relative to the grip portion 154.

FIG. 8 is a perspective view of showing the end cap 172 removed from the end sleeve 174. The annular wall 206 of the end sleeve 174 can be seen as well as the enlargements 208 on the proximal end of the filaments (not shown). A plurality of locking tabs 212 (also seen in FIG. 6C) extend proximally from the annular washer 202 secured to the grip portion 154 through openings 214 provided in the annular wall 206. Each of the locking tabs 212 can have a small radially inward tooth (not numbered) thereon that catches on the openings 214 and secures the end sleeve 174 on the proximal end of the grip portion 154. Because the locking tabs 212 are cantilevered and flexible, they can be cammed outward in a variety of ways to release the teeth from the openings 214, thus releasing the end sleeve 174 to move.

Rotation of the end cap 172 can cam the locking tabs 212 outward. For example, FIG. 8 shows an exemplary trilobular cam member 216 extending in a distal direction on the inside of the end cap 172. When assembled to the end of the end sleeve 174, the cam member 216 fits radially between the three locking tabs 212, as seen in FIG. 9A. Prior to rotation of the end cap 172 and displacement of the end sleeve 174, lesser radial portions of the cam member 216 are adjacent to or in contact with the locking tabs 212. Rotation of the end cap 172 by 60° causes the lobes of the trilobular cam member 216 to cam the locking tabs 212 outward, as seen in FIG. 9B. This releases the teeth on the locking tabs 212 from the openings 214 in the end sleeve 174, thus allowing the user to pull the end sleeve in a proximal direction, as seen in FIG. 7C. Once again, this causes the annular wall 206 to pull the enlargements 208 on the ends of the filaments 170 proximally, thus decoupling the deployment arms 108 from the pinch device buckle 60, as was seen in FIG. 5B.

While the invention has been described with reference to particular embodiments, it will be understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Features and components described with respect to one embodiment can be incorporated into other embodiments even if not expressly described with respect to that embodiment. Methods can include any of the steps recited or implicitly included herein, and the steps can be ordered in different ways. Therefore, it is intended that the invention not be limited to the particular embodiments disclosed herein, but that the invention will include all embodiments falling within the scope of the appended claims.

What is claimed is:

1. A prosthetic heart valve and delivery system, comprising:
    an expandable prosthetic heart valve having a constricted diameter and an expanded diameter;
    a delivery catheter having a distal end on which the heart valve is mounted;
    a pinch device separate from the heart valve that has an expanded state defining an annular frame formed around a central axis and having peaks and valleys extending in opposite axial directions around its periphery, the pinch device including an inner body covered with a biocompatible fabric covering, with a plurality of buckles integrated with the inner body and projecting from a proximal end without being covered by the fabric covering;
    an access system including a proximal handle and a distal access sheath, the handle and sheath defining a common lumen sized to allow passage therethrough of the distal end of the delivery catheter with the heart valve in its constricted diameter thereon, and the handle having one or more hemostatic seals to prevent blood leakage proximally past the distal end of the delivery catheter during use, the access system including a plurality of deployment arms extending from the proximal handle, wherein at least one of the plurality of deployment arms and the sheath are axially movable relative to the other, wherein each of the plurality of deployment arms is coupled to one of the buckles of the pinch device, and wherein, prior to delivery, the pinch device is positioned in a constricted state within a distal end of the access sheath and is distal with respect to the distal end of the delivery catheter, such that the pinch device can be expelled from the access sheath and self-expand prior to expansion of the heart valve while connected to the plurality of deployment arms; and
    wherein the handle includes an advancement mechanism for axially displacing the deployment arms in a distal direction, and a release mechanism comprising an end cap and an end sleeve for decoupling each deployment arm from its corresponding buckle, and wherein the end cap comprises an opening configured to allow the delivery catheter with the prosthetic heart valve mounted thereon in the constricted state to pass through the opening and into the handle,
    wherein the system is configured such that the distal access sheath can be introduced into the heart and advanced so that the distal end thereof is proximate a native heart valve, whereupon the pinch device can be expelled therefrom and positioned around native heart valve leaflets and the delivery catheter can be advanced through the access system to position the heart valve within the native heart valve leaflets such that expansion of the heart valve pinches the leaflets between the heart valve and pinch device.

2. The system of claim 1, wherein the plurality of buckles on the pinch device are located at terminal ends of three fingers extending in a proximal direction from the pinch device and distributed evenly around a periphery of the pinch device.

3. The system of claim 2, wherein the peaks of the pinch device project in a distal direction and the valleys project in a proximal direction, and the fingers extend proximally from three of the peaks of the pinch device.

4. The system of claim 2, wherein the peaks of the pinch device project in a proximal direction and the valleys project in a distal direction, and the fingers extend from three of the peaks distributed evenly around a periphery of the pinch device.

5. The system of claim 1, wherein the inner body includes circumferential struts connecting each two adjacent peaks and valleys each of which is generally S-shaped, with two curvatures separated by a point of inflection.

6. The system of claim 5, wherein each of the circumferential struts terminates at its corresponding peak and valley in an asymptotic manner such that it is nearly aligned with the vertical Z-axis.

7. The system of claim 1, wherein the access sheath comprises a plurality of channels through which the plurality of deployment arms extend, and a distal nose of the handle includes angled channels connected to the channels in the access sheath through which the plurality of deployment arms diverge radially outward in the handle.

8. The system of claim 1, wherein the proximal handle of the access system includes a distal housing and the advancement mechanism comprises a proximal grip portion slidably mounted over the distal housing in a telescoping fashion.

9. The system of claim 8, wherein the advancement mechanism comprises a thumb wheel mounted for rotation on the proximal grip portion that engages a gear rack fixed to the distal housing so as to advance the proximal grip portion.

10. A prosthetic heart valve and delivery system, comprising:
- a prosthetic heart valve movable between an expanded diameter and a constricted diameter;
- a delivery catheter having a distal end portion on which the prosthetic heart valve is mounted;
- a pinch device separate from the prosthetic heart valve, the pinch device being movable between an expanded state and a constricted state and comprising an annular frame having peaks and valleys extending in opposite axial directions around its periphery;
- an access system comprising a proximal handle, an access sheath, a plurality of deployment arms connected to and extending distally from the proximal handle, and one or more hemostatic seals disposed in the proximal handle, wherein the access sheath comprises a plurality of channels through which the plurality of deployment arms extend;
- wherein, prior to delivery, the pinch device is disposed within a distal end portion of the access sheath in the constricted state and wherein each of the plurality of deployment arms has a distal end portion releasably coupled to the pinch device such that the pinch device can be expelled from the access sheath and self-expand while connected to the plurality of deployment arms; and
- wherein the system is configured such that the distal access sheath can be introduced into the heart and advanced so that the distal end thereof is proximate a native heart valve, whereupon the pinch device can be expelled therefrom and positioned around native heart valve leaflets and the delivery catheter and the prosthetic heart valve can be advanced through the proximal handle, the one or more hemostatic seals, and the access sheath of the access system to position the prosthetic heart valve within the native heart valve leaflets such that expansion of the heart valve pinches the leaflets between the heart valve and pinch device.

11. The system of claim 10, wherein the deployment arms and the access sheath are axially movable relative to one another.

12. The system of claim 10, wherein the proximal handle comprises a grip portion and wherein the deployment arms are coupled to the grip portion such that axial motion of the grip portion results in axial motion of the deployment arms.

13. The system of claim 10, wherein the system is configured for use in a transapical delivery procedure.

14. A prosthetic heart valve and delivery system, comprising:
- an expandable pinch device movable between an expanded state and a constricted state, the pinch device comprising an annular frame having peaks and valleys extending in opposite axial directions around its periphery, the pinch device further comprising a plurality of buckles extending from the annular frame;
- an access system comprising a handle, an access sheath extending distally from the handle, and a plurality of deployment arms extending distally from the handle through the access sheath, the deployment arms being coupled to the pinch device, and the pinch device being positioned, prior to delivery, in a constricted state within a distal end portion of the access sheath such that the pinch device can be expelled from the access sheath and self-expand while connected to the plurality of deployment arms;
- wherein the handle includes an advancement mechanism for axially displacing the deployment arms and the pinch device when coupled to the deployment arms, and a release mechanism for decoupling each deployment arm for its corresponding buckle;
- a plurality of filaments, each filament paired with a corresponding deployment arm and having a distal end portion that nominally locks the corresponding deployment arm to a corresponding buckle and a proximal end portion connected to the release mechanism, wherein relative axial movement of the release mechanism with respect to the advancement mechanism pulls the filaments in a proximal direction, thereby de-coupling the buckles from the deployment arms;
- a delivery catheter having a distal end portion on which a prosthetic heart valve is mounted, the prosthetic heart valve being movable between an expanded state and a constricted state;
- wherein the system is configured such that the distal access sheath can be introduced into the heart and advanced so that the distal end thereof is proximate a native heart valve, whereupon the pinch device can be expelled therefrom and positioned around native heart valve leaflets and the delivery catheter and the prosthetic heart valve can be advanced through the handle and the access sheath of the access system to position the prosthetic heart valve within the native heart valve leaflets such that expansion of the heart valve pinches the leaflets between the heart valve and pinch device, and
- wherein the release mechanism comprises an opening configured to allow the delivery catheter with the prosthetic heart valve mounted thereon in the constricted state to pass through the opening and into the handle.

15. The system of claim 14, wherein the access system comprises one or more hemostatic seals disposed in the handle, wherein the one or more seals are configured to seal against an outer surface of the delivery catheter when the delivery catheter is advanced through the handle.

16. The system of claim 14, wherein the access sheath comprises a plurality of channels through which the plurality of deployment arms and filaments extend.

17. The system of claim 14, wherein the release mechanism is rotatable relative to the handle between an unlocked state and a locked state, and wherein when in the locked state the release mechanism is restrained from axial movement relative to the advancement mechanism and wherein when in unlocked state, the release mechanism can be moved axially relative to the advancement mechanism.

18. The system of claim 14, wherein each filament extends through a corresponding deployment arm.

19. A prosthetic heart valve and delivery system, comprising:
- an expandable pinch device movable between an expanded state and a constricted state, the pinch device comprising an annular frame having peaks and valleys extending in opposite axial directions around its periphery, the pinch device further comprising a plurality of buckles extending from the annular frame;
- an access system comprising a handle, an access sheath extending distally from the handle, and a plurality of deployment arms extending distally from the handle through the access sheath, the deployment arms being coupled to the pinch device, and the pinch device being positioned, prior to delivery, in a constricted state within a distal end portion of the access sheath such that the pinch device can be expelled from the access sheath and self-expand while connected to the plurality of deployment arms;

wherein the handle includes an advancement mechanism for axially displacing the deployment arms and the pinch device when coupled to the deployment arms, and a release mechanism for decoupling each deployment arm for its corresponding buckle, wherein the release mechanism is rotatable relative to the handle between an unlocked state and a locked state, and wherein when in the locked state the release mechanism is restrained from axial movement relative to the advancement mechanism and wherein when in unlocked state, the release mechanism can be moved axially relative to the advancement mechanism;

a plurality of filaments, each filament paired with a corresponding deployment arm and having a distal end portion that nominally locks the corresponding deployment arm to a corresponding buckle and a proximal end portion connected to the release mechanism, wherein relative axial movement of the release mechanism with respect to the advancement mechanism pulls the filaments in a proximal direction, thereby de-coupling the buckles from the deployment arms;

a delivery catheter having a distal end portion on which a prosthetic heart valve is mounted, the prosthetic heart valve being movable between an expanded state and a constricted state;

wherein the system is configured such that the distal access sheath can be introduced into the heart and advanced so that the distal end thereof is proximate a native heart valve, whereupon the pinch device can be expelled therefrom and positioned around native heart valve leaflets and the delivery catheter and the prosthetic heart valve can be advanced through the handle and the access sheath of the access system to position the prosthetic heart valve within the native heart valve leaflets such that expansion of the heart valve pinches the leaflets between the heart valve and pinch device.

20. The system of claim 19, wherein the release mechanism further includes a plurality of spring-loaded locking buttons to permit rotation relative to the handle between an unlocked state and a locked state.

* * * * *